(12) United States Patent
Skaar et al.

(10) Patent No.: US 8,263,642 B2
(45) Date of Patent: Sep. 11, 2012

(54) ANTIMICROBIAL COMPOUNDS AND METHODS OF USE THEREOF

(75) Inventors: Eric Skaar, Nashville, TN (US); Devin Stauff, Nashville, TN (US); Olusegun O. Aranmolate, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 313 days.

(21) Appl. No.: 12/491,988

(22) Filed: Jun. 25, 2009

(65) Prior Publication Data
US 2010/0004324 A1 Jan. 7, 2010

Related U.S. Application Data

(60) Provisional application No. 61/075,553, filed on Jun. 25, 2008.

(51) Int. Cl.
*A01N 43/32* (2006.01)
*C12N 1/38* (2006.01)
*C12Q 1/68* (2006.01)

(52) U.S. Cl. ........ 514/452; 514/615; 514/184; 424/404; 424/699; 435/244; 435/6.15

(58) Field of Classification Search .................. 514/452, 514/184; 435/244, 6.15; 424/404, 699
See application file for complete search history.

(56) References Cited

OTHER PUBLICATIONS

Torres et al. (Cell Host Microbe. 2007, vol. 1(2), pp. 109-119.*
Sams-Dodd (Drug discovery today, vol. 10, No. 2, 2005, pp. 139-147.*
Schafer et al. Drug Discovery Today 2008, 13 (21/22), 913-916.*
Horig et al. Journal of Translational Medicine 2004, 2(44.*

* cited by examiner

*Primary Examiner* — Savitha Rao
(74) *Attorney, Agent, or Firm* — Stites & Harbison PLLC; Mandy Wilson Decker

(57) ABSTRACT

In one aspect, the invention relates to compounds and methods useful for activating heme sensor systems; for decreasing virulence of bacteria, for example, *Staphylococcus aureus*; pharmaceutical compositions comprising the compounds; and methods of treating microbial-related disorders. This abstract is intended as a scanning tool for purposes of searching in the particular art and is not intended to be limiting of the present invention.

19 Claims, 9 Drawing Sheets

ANTIMICROBIAL COMPOUNDS AND METHODS OF USE THEREOF

CROSS-REFERENCE TO RELATED APPLICATIONS

This application claims the benefit of U.S. Provisional Application Ser. No. 61/075,553, filed Jun. 25, 2008, which is incorporated herein by reference in its entirety.

ACKNOWLEDGMENT

This invention was made with government support under U.S. Public Health Service Grant A169233 from the National Institute of Allergy and Infectious Diseases. The United States government has certain rights in the invention.

BACKGROUND

Recent research suggests that the frequency of antimicrobial resistance and its association with infectious diseases is increasing. Bacterial infections can occur in any subject, and many of such infections can be deadly. Nosocomial infections, for example, can be caused by strains of bacteria including deadly antimicrobial-resistant strains. In the United States alone, nosocomial infections are thought to contribute to or cause more than 77,000 deaths per year and cost approximately $5 to $10 billion annually. Among Gram-positive organisms, examples of resistant pathogens include resistant *Staphylococcus aureus*, β-lactam-resistant and multidrug-resistant *pneumococci*, and vancomycin-resistant *enterococci*. (Jones R N 2001 Chest 119 (supplement), 397S-404S: Resistance patterns among nosocomial pathogens: Trends over the past few years.)

The problem with bacterial infections and antibacterial resistance is compounded by the existence of bacterial strains resistant to multiple antibacterials. Thus, for at least this reason, there remains a need for new antimicrobials, particularly antimicrobials with different mechanisms of action.

SUMMARY

In accordance with the purpose(s) of the invention, as embodied and broadly described herein, the invention, in one aspect, relates to compounds useful as antibacterial compounds, and methods of treating disorders associated with bacterial infection.

In one aspect, the invention relates to methods for activating a heme sensor system in at least one bacterium comprising the step of contacting the at least one bacterium with an effective amount of a compound identified by a heme sensor system activator screen, thereby activating a heme efflux pump (HrtAB) in the at least one bacterium.

In a further aspect, the invention relates to methods for treating a bacterial infection in a mammal comprising the step of administering a therapeutically effective amount of a compound identified by a heme sensor system activator screen, thereby decreasing bacterial virulence in the mammal.

In a further aspect, the invention relates to methods for activating a heme sensor system in at least one bacterium comprising the step of contacting the at least one bacterium with an effective amount of a compound having a structure represented by a formula:

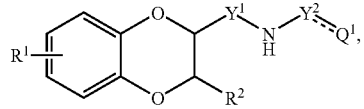

wherein $R^1$ comprises four substituents independently selected from hydrogen, hydroxyl, thiol, cyano, nitro, optionally substituted amino, azide, halide, and optionally substituted organic residue comprising from 1 to 4 carbons; wherein $R^2$ comprises two substituents independently selected from hydrogen, hydroxyl, thiol, cyano, nitro, optionally substituted amino, azido, halide, and optionally substituted organic residue comprising from 1 to 4 carbons; wherein $Y^1$ comprises carbonyl or $CR^3$, wherein $R^3$ comprises two substituents independently selected from hydrogen, and optionally substituted organic residue comprising from 1 to 4 carbons; wherein when --- is present, $Y^2$ comprises N; wherein when --- is absent, $Y^2$ comprises optionally substituted amino or optionally substituted methylene; and wherein $Q^1$ comprises optionally substituted C1-C18 alkyl, optionally substituted C1-C18 cycloalkyl, optionally substituted C1-C18 heteroalkyl, optionally substituted C1-C18 heterocycloalkyl; or a pharmaceutically acceptable derivative thereof; thereby activating a heme efflux pump (HrtAB) in the at least one bacterium.

In a further aspect, the invention relates to methods for treating a bacterial infection in a mammal comprising the step of administering a therapeutically effective amount of a compound having a structure represented by a formula:

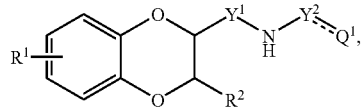

wherein $R^1$ comprises four substituents independently selected from hydrogen, hydroxyl, thiol, cyano, nitro, optionally substituted amino, azide, halide, and optionally substituted organic residue comprising from 1 to 4 carbons; wherein $R^2$ comprises two substituents independently selected from hydrogen, hydroxyl, thiol, cyano, nitro, optionally substituted amino, azido, halide, and optionally substituted organic residue comprising from 1 to 4 carbons; wherein $Y^1$ comprises carbonyl or $CR^3$, wherein $R^3$ comprises two substituents independently selected from hydrogen, and optionally substituted organic residue comprising from 1 to 4 carbons; wherein when --- is present, $Y^2$ comprises N; wherein when --- is absent, $Y^2$ comprises carbonyl, optionally substituted amino, or optionally substituted methylene; and wherein $Q^1$ comprises optionally substituted C1-C18 alkyl, optionally substituted C1-C18 cycloalkyl, optionally substituted C1-C18 heteroalkyl, optionally substituted C1-C18 heterocycloalkyl; or a pharmaceutically acceptable derivative thereof, thereby decreasing bacterial virulence in the mammal.

In a further aspect, the invention relates to methods for activating a heme sensor system in at least one bacterium comprising the step of contacting the at least one bacterium with an effective amount of a compound having a structure represented by a formula:

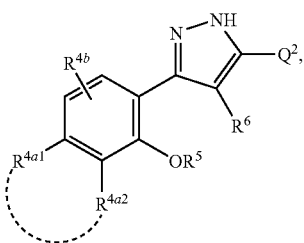

wherein --- is an optionally bond; wherein $R^{4a1}$ and $R^{4a2}$ are independently selected from hydrogen, hydroxyl, thiol, cyano, nitro, optionally substituted amino, azide, halide, and optionally substituted organic residue comprising from 1 to 10 carbons; wherein $R^{4b}$ comprises two substituents independently selected from hydrogen, hydroxyl, thiol, cyano, nitro, optionally substituted amino, azide, halide, and optionally substituted organic residue comprising from 1 to 4 carbons; wherein $R^5$ comprises hydrogen or optionally substituted organic residue comprising from 1 to 4 carbons; wherein $R^6$ comprises hydrogen or optionally substituted organic residue comprising from 1 to 4 carbons; and wherein $Q^2$ comprises optionally substituted C1-C18 alkyl, optionally substituted C1-C18 cycloalkyl, optionally substituted C1-C18 heteroalkyl, or optionally substituted C1-C18 heterocycloalkyl; or a pharmaceutically acceptable derivative thereof, thereby activating a heme efflux pump (HrtAB) in the at least one bacterium.

In a further aspect, the invention relates to methods for treating a bacterial infection in a mammal comprising the step of administering a therapeutically effective amount of a compound having a structure represented by a formula:

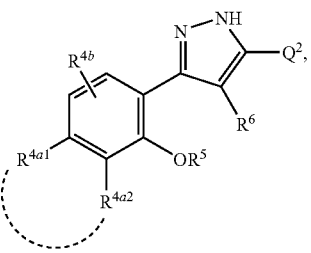

wherein --- is an optionally bond; wherein $R^{4a1}$ and $R^{4a2}$ are independently selected from hydrogen, hydroxyl, thiol, cyano, nitro, optionally substituted amino, azide, halide, and optionally substituted organic residue comprising from 1 to 10 carbons; wherein $R^{4b}$ comprises two substituents independently selected from hydrogen, hydroxyl, thiol, cyano, nitro, optionally substituted amino, azide, halide, and optionally substituted organic residue comprising from 1 to 4 carbons; wherein $R^5$ comprises hydrogen or optionally substituted organic residue comprising from 1 to 4 carbons; wherein $R^6$ comprises hydrogen or optionally substituted organic residue comprising from 1 to 4 carbons; and wherein $Q^2$ comprises optionally substituted C1-C18 alkyl, optionally substituted C1-C18 cycloalkyl, optionally substituted C1-C18 heteroalkyl, or optionally substituted C1-C18 heterocycloalkyl; or a pharmaceutically acceptable derivative thereof, thereby decreasing bacterial virulence in the mammal.

In a further aspect, the invention relates to methods for activating a heme sensor system in at least one bacterium comprising the step of contacting the at least one bacterium with an effective amount of a Vitamin K, thereby activating a heme efflux pump (HrtAB) in the at least one bacterium.

In a further aspect, the invention relates to methods for treating a bacterial infection in a mammal comprising the step of administering a therapeutically effective amount of a Vitamin K, thereby decreasing bacterial virulence in the mammal.

In a further aspect, the invention relates to methods for treating a bacterial infection in a mammal comprising the step of co-administering a therapeutically effective amount of a heme sensor system activator and a therapeutically effective amount of one or more antimicrobial agents, thereby treating the infection in the mammal.

In a further aspect, the invention relates to kits comprising a therapeutically effective amount of a heme sensor system activator and a therapeutically effective amount of one or more antimicrobial agents.

In a further aspect, the invention relates to pharmaceutical compositions comprising a therapeutically effective amount of a heme sensor system activator and a pharmaceutically acceptable carrier.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
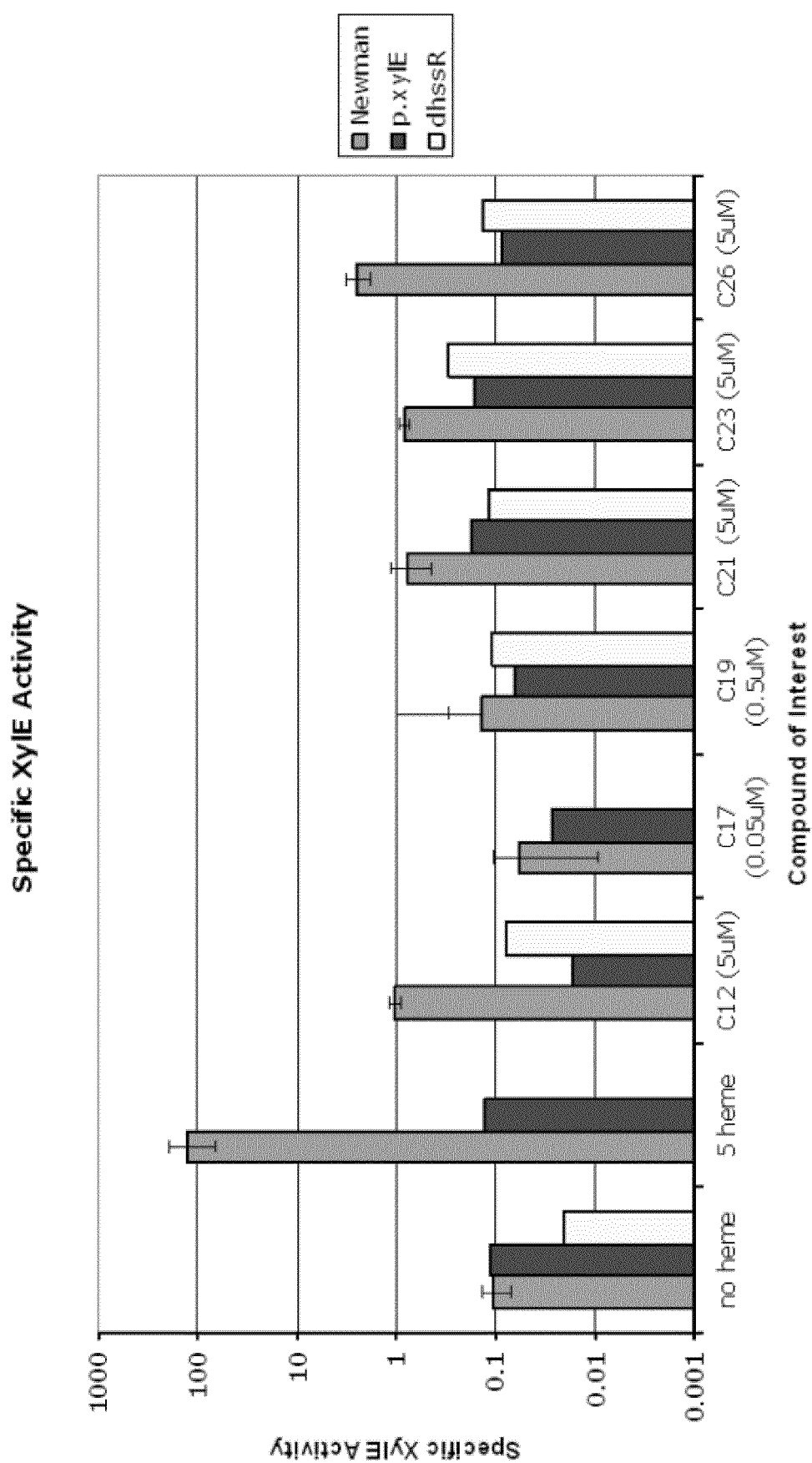
FIG. 1 shows a plot of specific XylE activity for various disclosed compounds.
Figure 2:
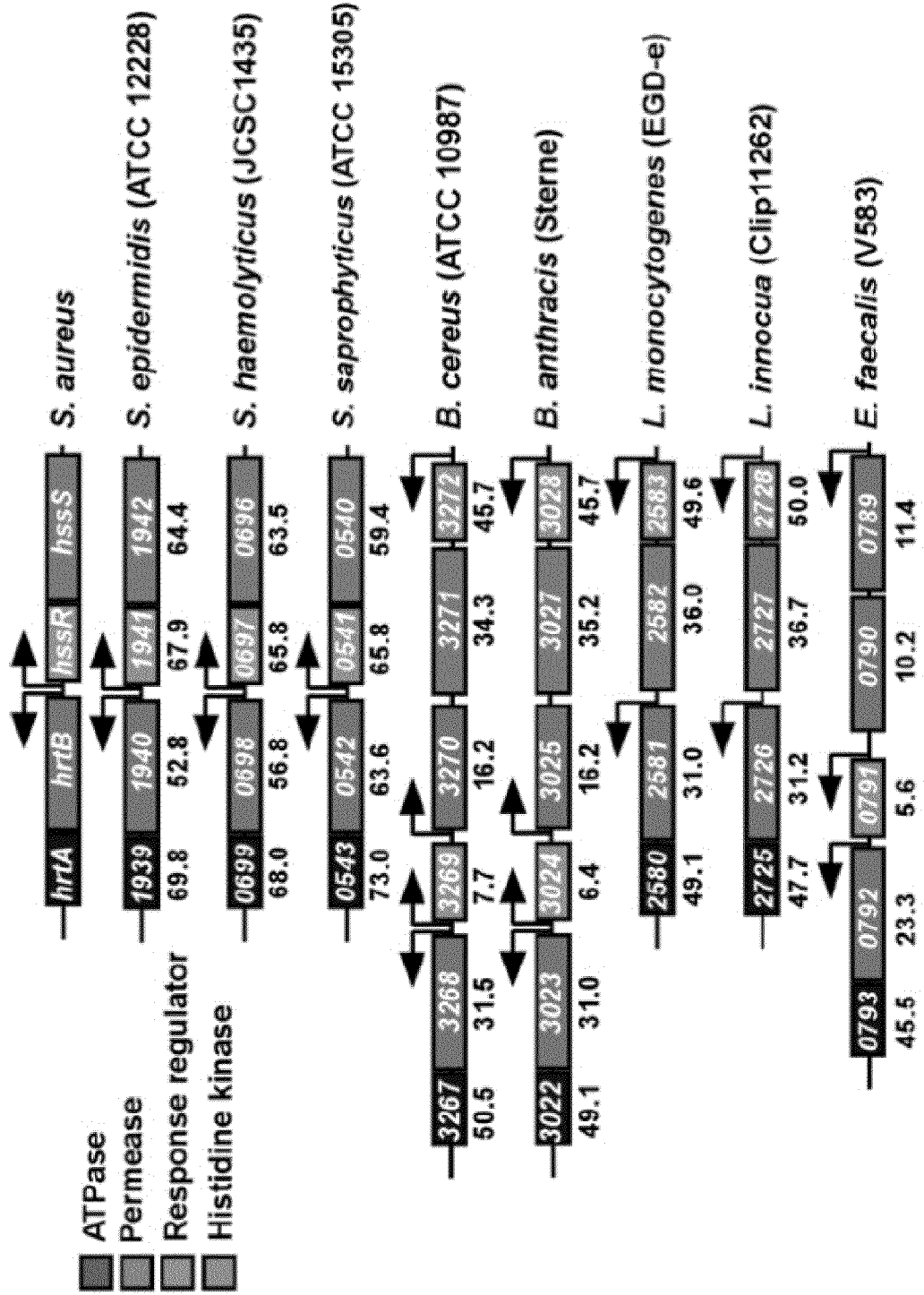
FIG. 2 shows that the alignment of genomic sequences among Gram-positive bacteria that contain orthologous hrtAB and HssRS systems. The numbers within each box represent corresponding gene numbers in the listed annotation. The numbers underneath each gene correspond to the percent amino acid identity to the representative S. aureus genes. Arrows denote the predicted direction of transcription.
Figure 3:
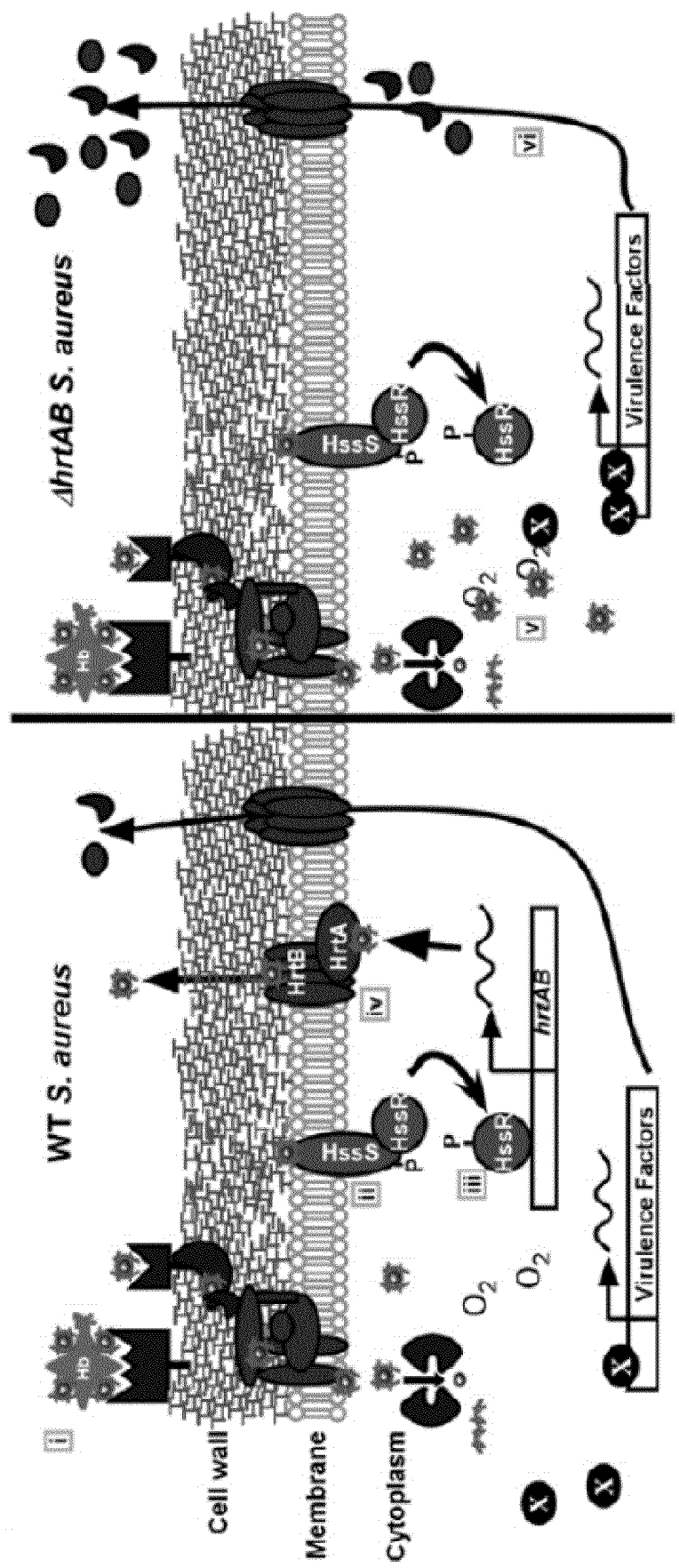
FIG. 3 shows a diagram depicting the activation and inactivation of the heme sensor system and effects thereof. In S. aureus, for example, heme internalized through cell-wall-anchored proteins (i), is sensed by HssS, which subsequently activates HssR (ii). HssR then binds the promoter region upstream of hrtAB (iii), leading to increased expression and elaboration of the HrtAB efflux pump (iv). HrtAB then pumps surplus cytoplasmic heme out of the bacterium. (C) Inactivation of hrtAB leads to the cytoplasmic accumulation of heme, which increases cellular stress (v). Staphylococcal stress-sensing systems are activated, leading to an increase in the expression and/or secretion of virulence factors, including exotoxin-3, -5, and -8, Map-w, fibronectin-binding protein, and FLIPr (vi), which increase liver-specific hypervirulence through inhibiting immune cell recruitment.
Figure 4:
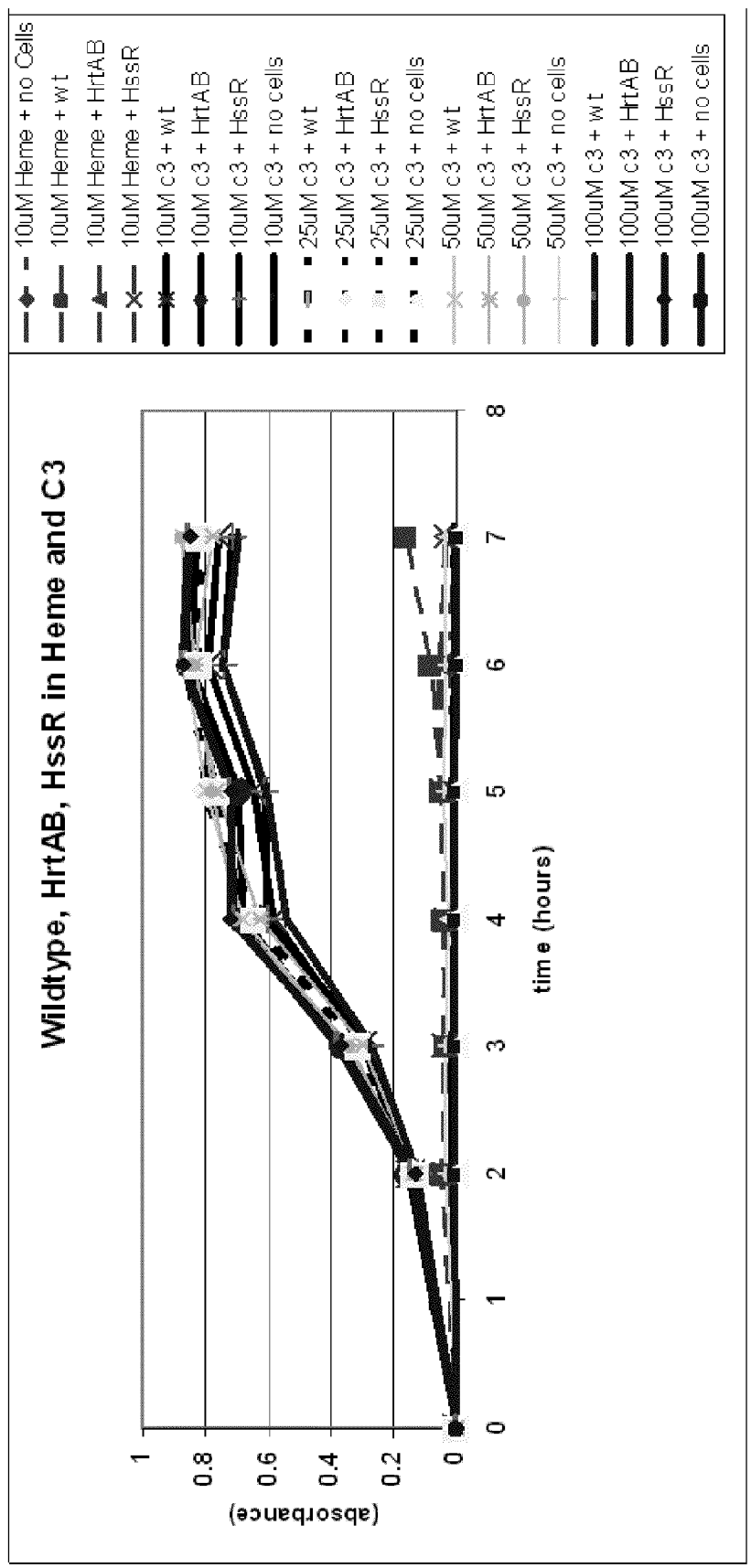
FIG. 4 shows a plot of absorbance vs. time for Compound 3 (C3) in a disclosed assay experiment.
Figure 5:
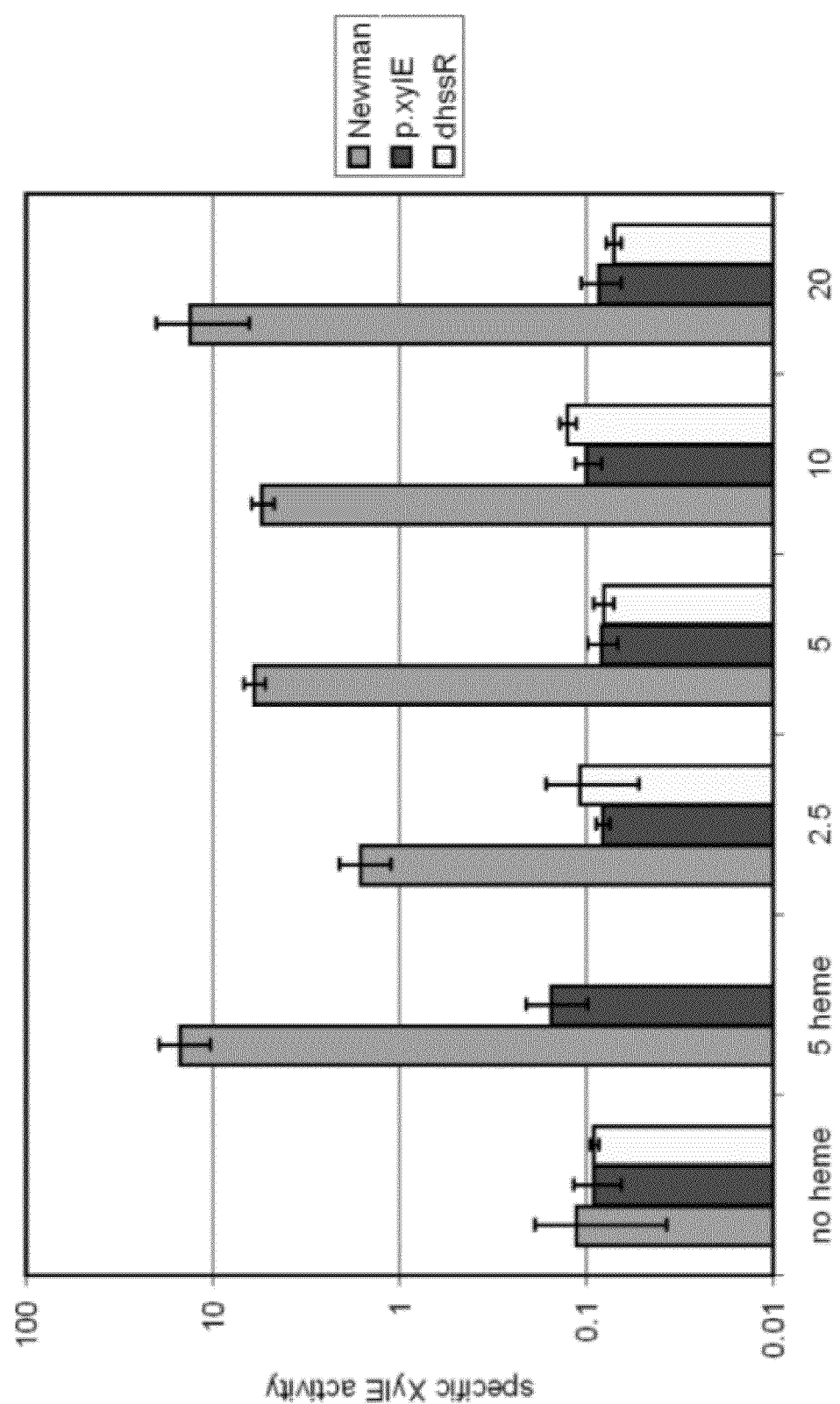
FIG. 5 shows a plot of specific XylE activity for Compound 3 (C3), as defined hereinbelow.
Figure 6:
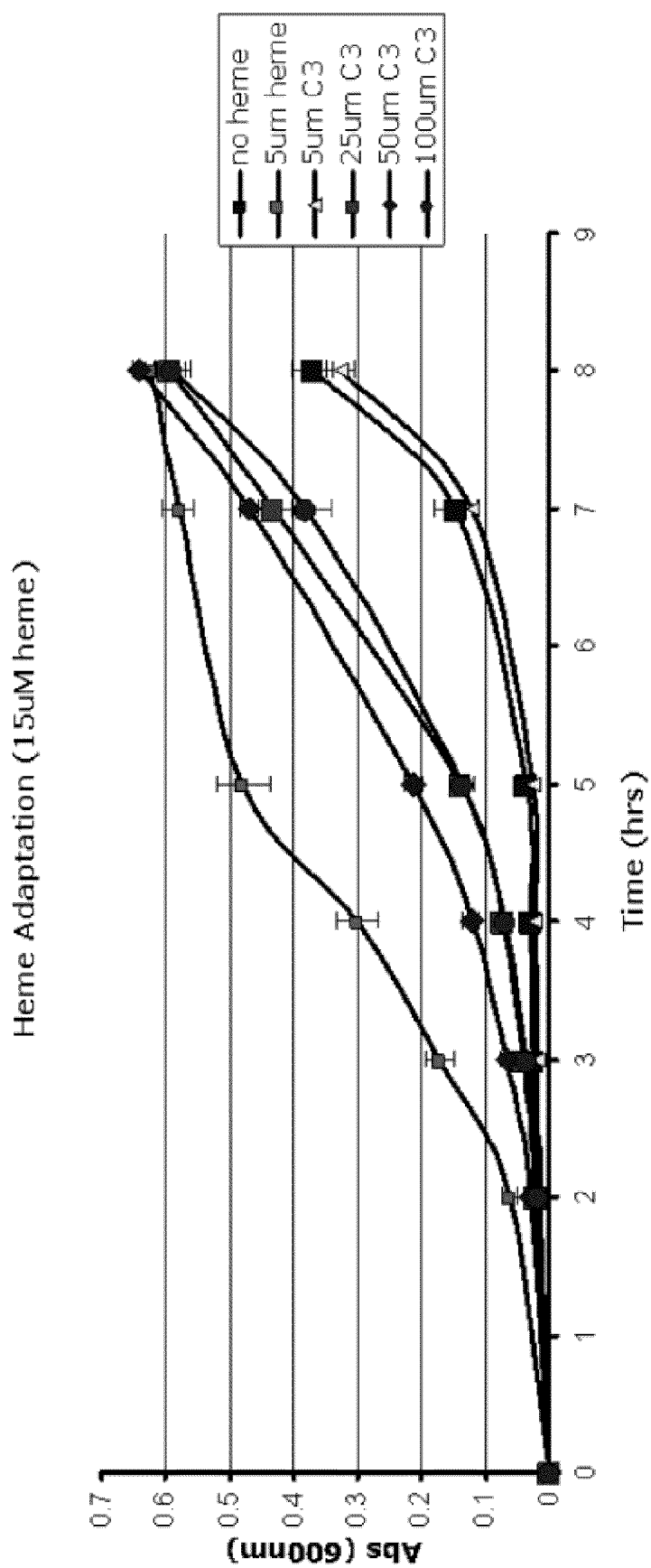
FIG. 6 shows a plot displaying heme adaptation of Compound 3 (CS), as defined hereinbelow.
Figure 7:
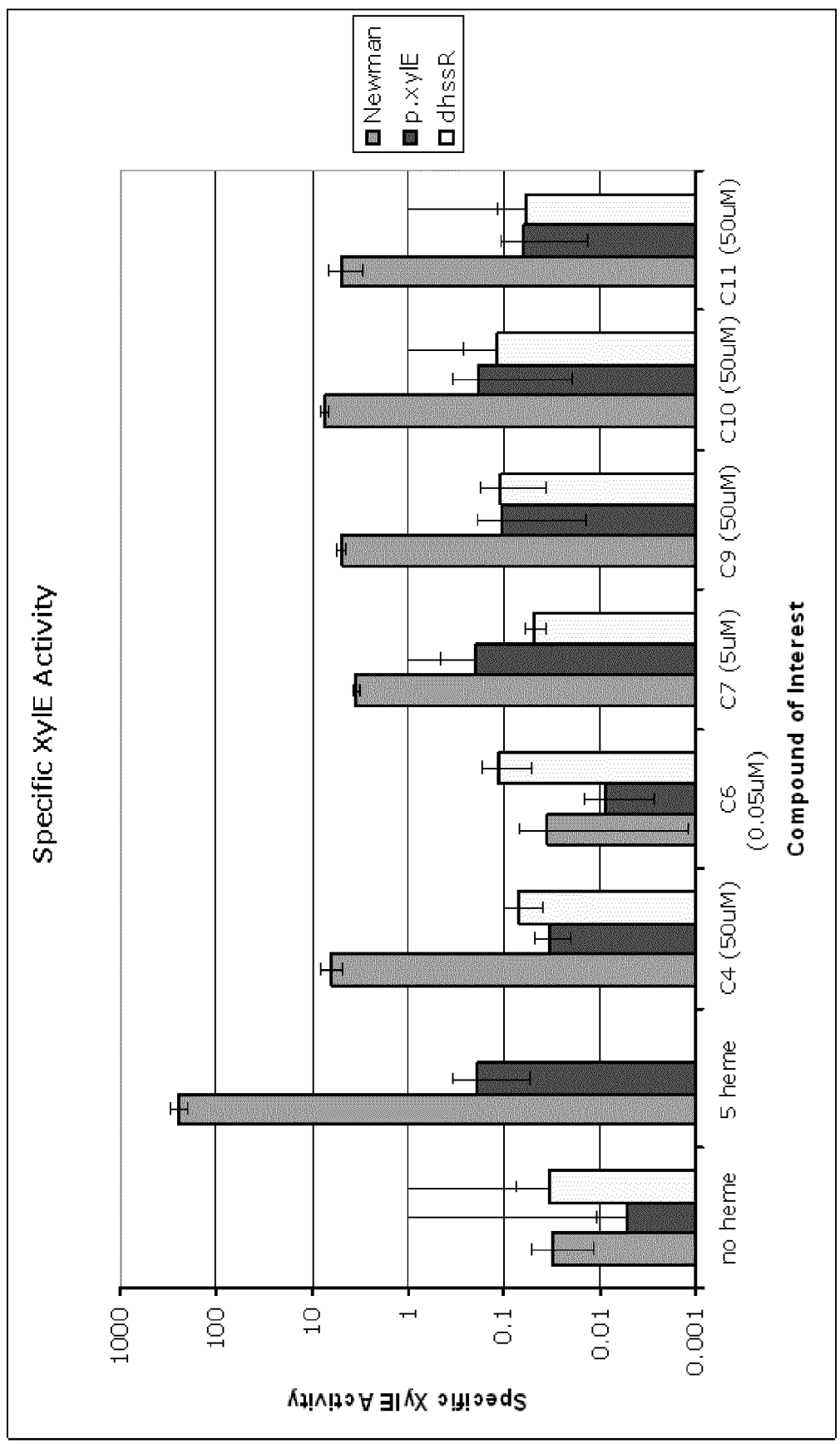
FIG. 7 shows a plot of specific XylE activity for various disclosed compounds.
Figure 8:
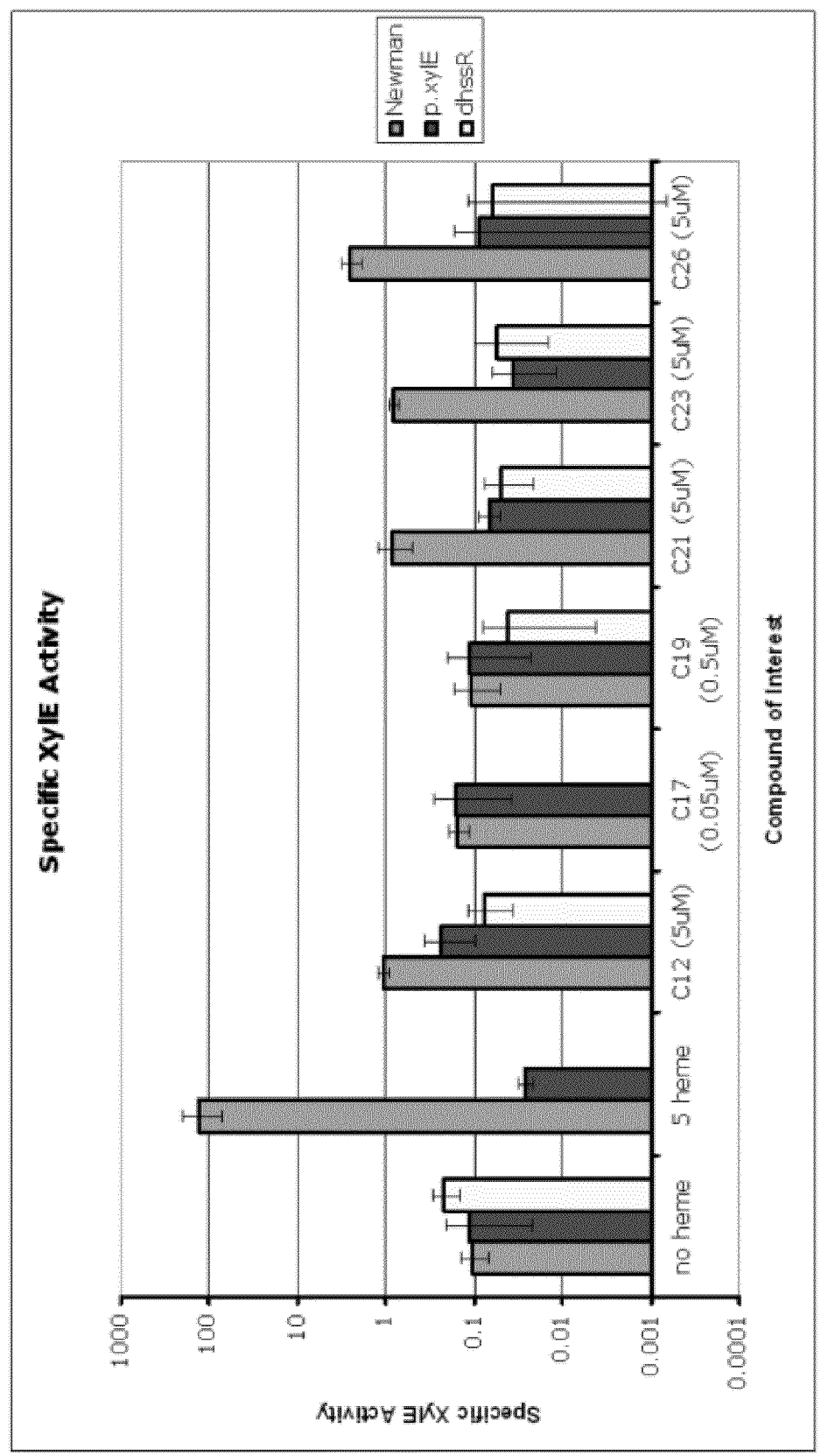
FIG. 8 shows a plot of specific XylE activity for various disclosed compounds.
Figure 9:
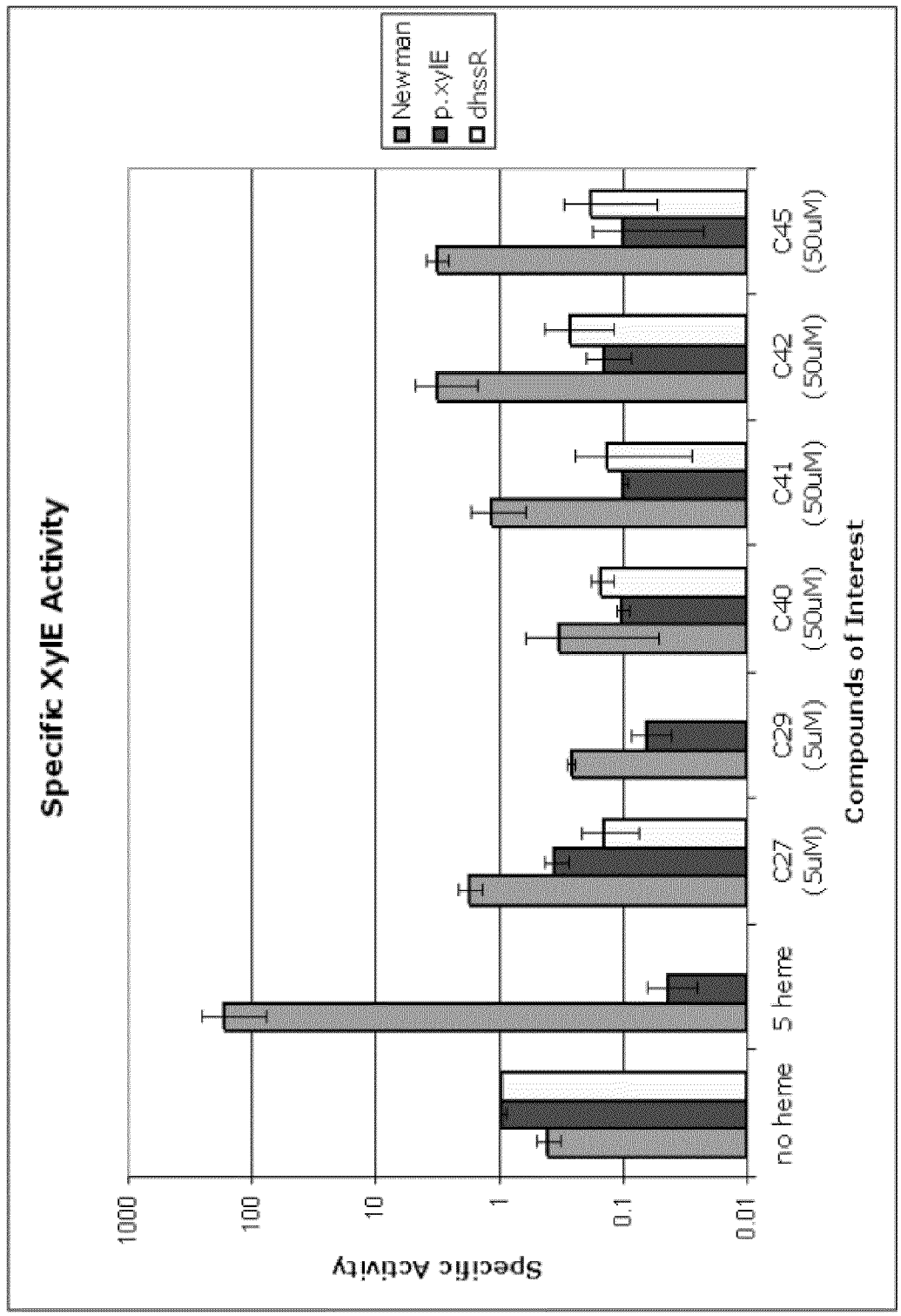
FIG. 9 shows a plot of specific XylE activity for various disclosed compounds.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can need to be independently confirmed.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the terms "optional" or "optionally" means that the subsequently described event or circumstance can or can not occur, and that the description includes instances where said event or circumstance occurs and instances where it does not.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

By "prevent" or "preventing" is meant to preclude, avert, obviate, forestall, stop, or hinder something from happening, especially by advance action. It is understood that where reduce, inhibit or prevent are used herein, unless specifically indicated otherwise, the use of the other two words is also expressly disclosed.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, a "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. The term "optionally substituted," means that the compound, atom, or residue can or cannot be substituted, as defined herein.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, 1 to 20 carbons, 1 to 18 carbons, 1 to 16 carbons, 1 to 14 carbons, 1 to 10 carbons, 1 to 8 carbons, 1 to 6 carbons, 1 to 4 carbons, 1 to 3 carbons, or 1 to 2 carbons, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —$OC(O)A^1$ or —$C(O)OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -$(AO(O)C-A^2-C(O)O)_a$ or -$(AO(O)C-A^2-OC(O))_a$-, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula $-(A^1O-A^2O)_a-$, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

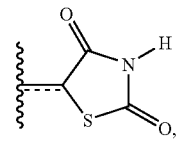

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. IRON LIMITATION IN BACTERIA

In one aspect, the disclosed methods and compositions are directed to the treatment of disorders associated with bacteria, e.g., bacterial infections. In a further aspect, the disclosed methods and compositions can be useful for the modulation of a newly identified heme sensor system present in bacteria. In a still further aspect, the disclosed methods and compositions can modulate (e.g., activate) the heme sensor system, thereby decreasing bacterial virulence.

It should be appreciated that one obstacle that bacterial pathogens encounter when infecting vertebrates is iron limitation. Iron is a cofactor involved in many biochemical processes and thus can be useful to many pathogenic bacteria for the establishment of infection (Bullen, J. J., and Griffiths, E. (1999). Iron and Infection: Molecular, Physiological and Clinical Aspects (New York: John Wiley and Sons). The majority of vertebrate iron is in the form of the metalloporphyrin heme, the functional cofactor of hemoglobin and myoglobin, the oxygen transport and storage proteins of blood and muscle, respectively (Deiss, A. 1983 "Iron metabolism in reticuloendothelial cells." Semin. Hematol. 20, 81-90). Transcription profiling-based identification of *Staphylococcus aureus* genes regulated by the agr and/or sarA loci. (J. Bacteriol. 183, 7341-7353.). *S. aureus*, for example, acquire heme through the elaboration of transport systems which rapidly transport host-derived heme into the *staphylococcal* cytoplasm for use as a nutrient source (Skaar, E. P., Humayun, M., Bae, T., DeBord, K. L., and Schneewind, O. 2004). "Iron-source preference of *Staphylococcus aureus* infections." Science 305, 1626-1628). While not wishing to be bound by theory, in one aspect, *Staphylococci* likely facilitate this process through the hemolysin-mediated rupture of erythrocytes upon entry into the blood stream (Skaar, E. P., Humayun, M., Bae, T., DeBord, K. L., and Schneewind, O. 2004).

Although heme is a valuable nutrient source to invading pathogens, the intracellular accumulation of heme can be toxic due to heme's reactivity. Therefore, organisms that acquire exogenous heme to satisfy nutrient iron needs can have adaptable mechanisms to avoid surplus heme accumulation. In this regard, recently reported was the identification of a subset of *staphylococcal* proteins that are affected by changes in environmental hemin (the oxidized form of heme) concentration. In particular, exposure to exogenous hemin results in the up-regulation of the Heme Regulated Transporter, HrtAB (Friedman, D. B., Stauff, D. L., Pishchany, G., Whitwell, C. W., Torres, V. J., and Skaar, E. P. (2006). "*Staphylococcus aureus* Redirects Central Metabolism to Increase Iron Availability." PLoS Pathog. 2). The up-regulation of HrtAB upon exposure to hemin suggests that bacteria, e.g., *S. aureus*, possess systems capable of sensing heme and subsequently altering protein expression. The association of heme with the major protein constituents of blood and muscle establishes heme as a molecular marker that can potentially be exploited by bacteria to distinguish internal host tissue from surface colonization sites.

Recently, a bacterial TCS, called the Heme-Sensor System (HssRS), was identified. HssRS can respond to heme exposure and can activate the expression of HrtAB, an efflux pump that at least plays a role in intracellular heme homeostasis. It was found that inactivation of the Hss or Hrt systems results in enhanced liver-specific *S. aureus* virulence which can correlate with a reduced innate immune response to infection. *Staphylococcal* strains unable to sense and excrete surplus heme can exhibit increased virulence factor expression and secretion, providing a mechanistic explanation for the observed immunomodulation. It will be appreciated that Hss and Hrt systems are present in, *Bacillus anthracis, Listeria monocytogenes, Staphylococcus epidermidis*, and *Enterococcus faecalis*, to name a few non-limiting examples.

Examination of the genomic context immediately adjacent to the hrtAB locus revealed the presence of two genes predicted to encode for a TCS. This TCS designation is based on BLAST analyses which revealed that the closest annotated matches to these genes are the response regulator ompR (e-value $6 \times 10^{-55}$) and histidine kinase baeS (e-value $8 \times 10^{-32}$) of *Escherichia coli*. TCS can sense environmental stimuli and regulate gene expression. On the basis of studies described below, this newly identified TCS was named the Heme Sensor System Regulator and Sensor, HssRS (HssR-response regulator, HssS-histidine kinase). The predicted protein product of HssS comprises two transmembrane regions flanking an extra-cytoplasmic ligand sensing domain. The cytoplasmic portion of HssS can be predicted to be comprised of a HisKA dimerization/phosphoacceptor region linked to an ATPase domain. BLAST analyses of full-length HssS as well as the predicted sensor domain demonstrate that the protein is conserved across many Gram positive bacteria. To evaluate the possibility that the heme-dependent expression of hrtAB is mediated by HssRS, isogenic mutant strains were generated in which either hssR or hssS were deleted (ΔhssR, ΔhssS). Growth curve analyses indicated that both HssR and HssS can be useful for *S. aureus* adaptation to heme toxicity, a phenotype that was complemented by introducing a wildtype copy of hssR in trans into ΔhssR. These data demonstrate that both HrtAB and HssRS can be useful for bacterial heme adaptation.

Genomic analyses of the hrt and hss loci indicate that these systems are conserved across Gram positive bacteria, including, but not limited to, the important human pathogens *Staphylococcus epidermidis, Bacillus anthracis, Listeria monocytogenes*, and *Enterococcus faecalis*. Thus, the disclosed methods and compositions can be useful in treating a number of disorders associated with bacterial infections, e.g., gram-positive bacterial infections.

C. COMPOUNDS

In one aspect, the invention relates to compounds useful as antimicrobial agents. More specifically, the present invention relates to compounds that modulate the heme sensor system, HssRS, thereby affecting bacterial virulence. The compounds of the invention are useful in the treatment of disorders associated with bacterial infections, as further described herein.

In a further aspect, the compound is identified from members of the ChemBridge Library and/or the ChemDiv Library.

In one aspect, the compound comprises one or more of an optionally substituted 2,3-dihydrobenzo[b][1,4]dioxine residue or an optionally substituted 3-phenyl-1H-pyrazole residue.

In a specific aspect, the compound can be present as: the compound is present as: N-(1-(2,3-dihydrobenzo[b][1,4]dioxin-2-yl)ethyl)-1-phenylcyclopentanecarboxamide; 3-bromo-5-(furan-2-yl)-N-(2-hydroxy-5-methylphenyl)-7-(trifluoromethyl)-4,5,6,7-tetrahydropyrazolo[1,5-α]pyrimidine-2-carboxamide; 5-methoxy-2-(5-p-tolyl-1H-pyrazol-3-yl)phenol; 5-methoxy-2-(5-(4-methoxyphenyl)-1H-pyrazol-3-yl)phenol; 2-(4-methoxybenzamido)-5-phenylthiophene-3-carboxamide; 1-(4-fluorobenzyl)-3-(4-phenoxyphenyl)thiourea; N-(4-(benzo[d]oxazol-2-yl)phenyl)-3-methylbenzamide; (E)-N'-((5-(4-bromophenyl)furan-2-yl)methylene)-2,3-dihydrobenzo[b][1,4]dioxine-2-carbohydrazide; (E)-N'-((5-(3-(trifluoromethyl)phenyl)furan-2-yl)methylene)-2,3-dihydrobenzo[b][1,4]dioxine-2-carbohydrazide; 3-(5-(furan-2-yl)-1H-pyrazol-3-yl)naphthalen-1-ol; (Z)—N-(4-chlorophenyl)-2-(2-oxo-3-(4-oxo-3-propyl-2-thioxothiazolidin-5-ylidene)indolin-1-yl)acetamide; 2-(5-phenyl-4,5-dihydro-1H-pyrazol-3-yl)-1H-indene-1,3(2H)-dione; 4-(2,4-dichlorophenoxy)-N-(4-sulfamoylphenyl)butanamide; (E)-N-(4-iodophenyl)-3-(5-nitrothiophen-2-yl)acrylamide; or 5-bromo-N-(2-hydroxy-4,5-dimethylphenylcarbamothioyl)-2-methoxybenzamide.

In a further specific aspect, the compound is present as:

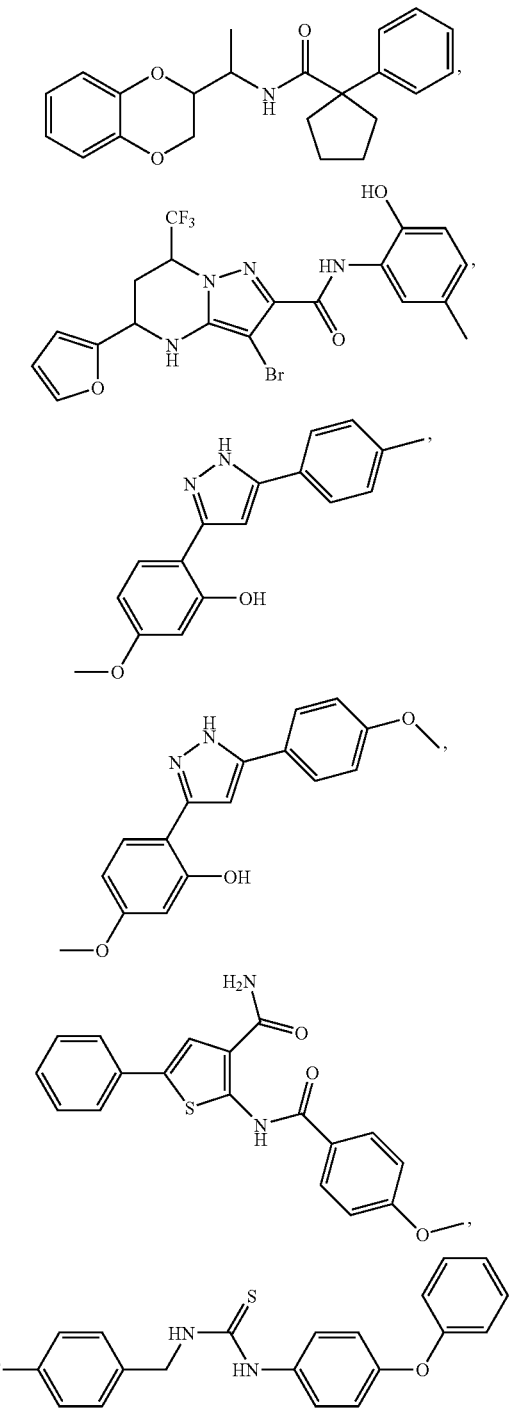

17
-continued

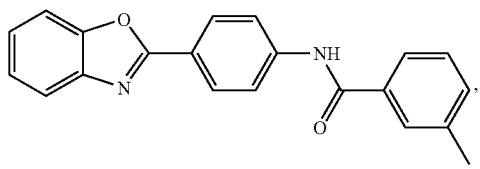

18
-continued

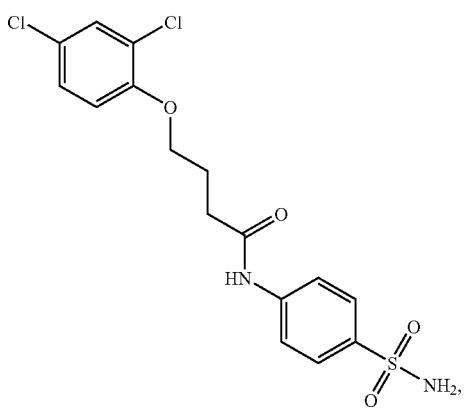

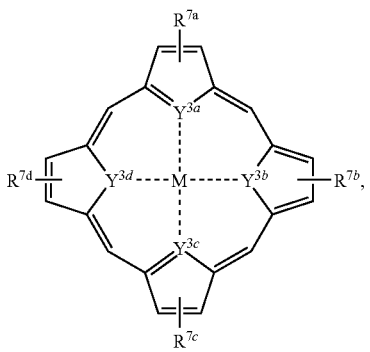

In one aspect, the compound is chelated to at least one metal. For example, the at least one metal can be selected from Ga, Gd, Fe, In, Pd, Pt, Ru, Mn, Sn, Zn, Mg, Ti, Co, and Cr.

In yet another aspect, the compound is not a metalloporphyrin analogue. As used herein, a metalloporphyrin analogue can have a structure represented by a formula:

wherein each $R^{7a}$, $R^{7b}$, $R^{7c}$, and $R^{7d}$ comprises two substituents independently selected from hydrogen, hydroxyl, thiol, cyano, nitro, optionally substituted amino, azide, halide, and optionally substituted organic residue comprising from 1 to 4 carbons; wherein each - - - is an optional bond; wherein M, if present, is a metal selected from Ga, Gd, Fe, In, Pd, Pt, Ru, Mn, Sn, Zn, Mg, Ti, Co, and Cr; wherein each $Y^{3a}$, $Y^{3b}$, $Y^{3c}$, and $Y^{3d}$ independently comprises N or NH.

In one aspect, a disclosed compound can have a structure represented by a formula:

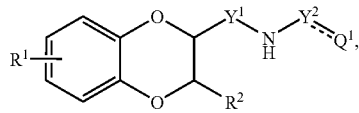

wherein $R^1$ comprises four substituents independently selected from hydrogen, hydroxyl, thiol, cyano, nitro, optionally substituted amino, azide, halide, and optionally substituted organic residue comprising from 1 to 4 carbons; wherein $R^2$ comprises two substituents independently selected from hydrogen, hydroxyl, thiol, cyano, nitro, optionally substituted amino, azide, halide, and optionally substituted organic residue comprising from 1 to 4 carbons; wherein $Y^1$ comprises carbonyl or $CR^3$, wherein $R^3$ comprises two substituents independently selected from hydrogen, and optionally substituted organic residue comprising from 1 to 4 carbons; wherein when ---is present, $Y^2$ comprises N; wherein when ---is absent, $Y^2$ comprises optionally substituted amino or optionally substituted methylene; and wherein $Q^1$ comprises optionally substituted C1-C18 alkyl, optionally substituted C1-C18 cycloalkyl, optionally substituted C1-C18 heteroalkyl, optionally substituted C1-C18 heterocycloalkyl; or a pharmaceutically acceptable derivative thereof In one aspect, each $R^1$ independently comprises hydrogen.

In a further aspect, $Y^1$ comprises carbonyl. In yet a further aspect, $Y^1$ comprises $CR^3$, wherein one $R^3$ comprises hydrogen and the other $R^3$ comprises methyl, ethyl, propyl, or butyl.

In one aspect, wherein ---is present, $Y^2$ comprises N. In a further aspect, wherein ---is absent, $Y^2$ comprises NH. In still a further aspect, wherein ---is absent, $Y^2$ comprises carbonyl.

In one aspect, $Q^1$ comprises optionally substituted cycloalkyl, optionally substituted heterocycloalkyl, optionally substituted aryl, or optionally substituted heteroaryl. In a further aspect, $Q^1$ comprises aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, arylthio, heteroarylthio, arylthioalkyl, alkoxyarylthio, alkylcarbonyl, arylcarbonyl, alkylaminocarbonyl, arylaminocarbonyl, arylcarbonylamino, arylsulfinyl, arylsulfinylalkyl, arylsulfonylamino, or arylsulfonaminocarbonyl.

In a further aspect, $Q^1$ comprises optionally substituted cyclopentyl, optionally substituted furanyl, optionally substituted piperadyl, optionally substituted pyridyl, or optionally substituted thiophenyl.

In a still further aspect, $Q^1$ comprises a residue having a structure represented by a formula:

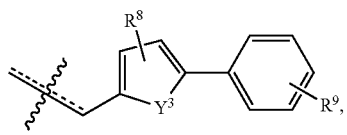

wherein $Y^3$ is O or S; wherein $R^8$ comprises two substituents independently selected from hydrogen, hydroxyl, thiol, cyano, nitro, optionally substituted amino, azido, halide, and optionally substituted organic residue comprising from 1 to 4 carbons; and wherein $R^9$ comprises five substituents independently selected from hydrogen, hydroxyl, thiol, cyano, nitro, optionally substituted amino, azido, halide, and optionally substituted organic residue comprising from 1 to 4 carbons.

In a specific aspect, $Q^1$ is present as:

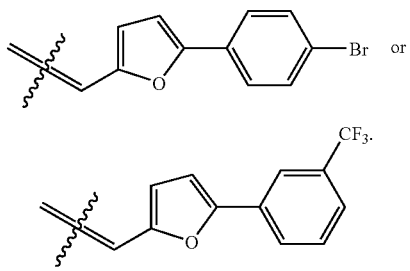

In a further aspect, $Q^1$ comprises a residue having a structure represented by a formula:

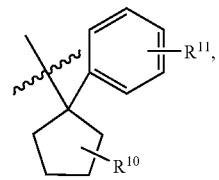

wherein $R^{10}$ comprises eight substituents independently selected from hydrogen, hydroxyl, thiol, cyano, nitro, optionally substituted amino, azido, halide, and optionally substituted organic residue comprising from 1 to 4 carbons; and wherein $R^{11}$ comprises five substituents independently selected from hydrogen, hydroxyl, thiol, cyano, nitro, optionally substituted amino, azido, halide, and optionally substituted organic residue comprising from 1 to 4 carbons.

In one aspect, $Q^1$ is present as:

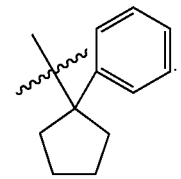

In a further aspect, the compound has a structure represented by a formula:

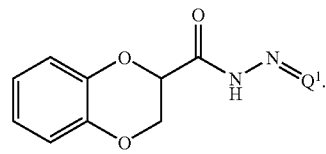

In a specific aspect, the compound is present as:

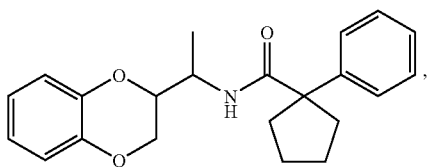

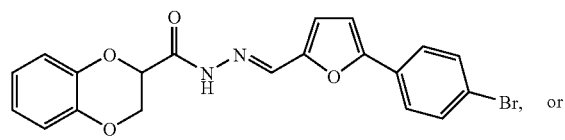

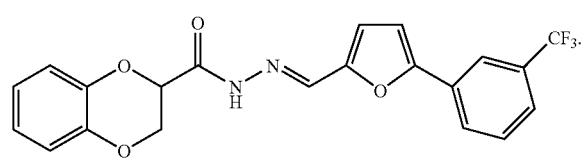

In one aspect, a disclosed compound can have a structure represented by a formula:

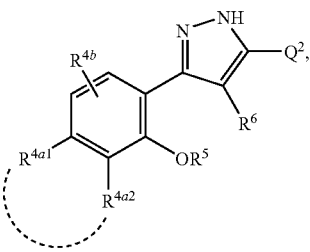

wherein ---is an optionally bond; wherein $R^{4a1}$ and $R^{4a2}$ are independently selected from hydrogen, hydroxyl, thiol, cyano, nitro, optionally substituted amino, azide, halide, and optionally substituted organic residue comprising from 1 to 10 carbons; wherein $R^{4b}$ comprises two substituents independently selected from hydrogen, hydroxyl, thiol, cyano, nitro, optionally substituted amino, azide, halide, and optionally substituted organic residue comprising from 1 to 4 carbons; wherein $R^5$ comprises hydrogen or optionally substituted organic residue comprising from 1 to 4 carbons; wherein $R^6$ comprises hydrogen or optionally substituted organic residue comprising from 1 to 4 carbons; and wherein $Q^2$ comprises optionally substituted C1-C18 alkyl, optionally substituted C1-C18 cycloalkyl, optionally substituted C1-C18 heteroalkyl, or optionally substituted C1-C18 heterocycloalkyl; or a pharmaceutically acceptable derivative thereof.

In a further aspect, $Q^2$ comprises C1-C12 cycloalkyl or C1-C12 heterocycloalkyl. In a still further aspect, $Q^2$ comprises aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, arylthio, heteroarylthio, arylthioalkyl, alkoxyarylthio, alkylcarbonyl, arylcarbonyl, alkylaminocarbonyl, arylaminocarbonyl, arylcarbonylamino, arylsulfinyl, arylsulfinylalkyl, arylsulfonylamino, or arylsulfonaminocarbonyl.

In yet another aspect, $Q^2$ comprises optionally substituted benzyl, furanyl, thiophenyl, pyridyl, or piperadyl. In a specific aspect, $Q^2$ is a residue having a structure represented by a formula:

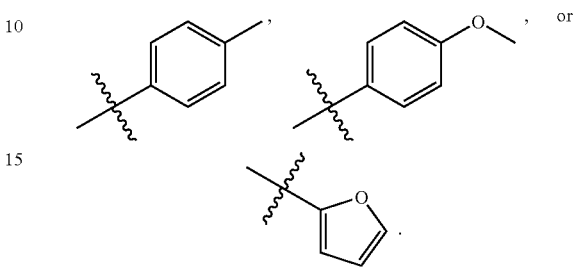

In one aspect, each $R^{4b}$ is hydrogen.
In a further aspect, $R^{4a1}$ is alkoxy. In a still further aspect, $R^{4a1}$ is methoxy, ethoxy, propoxy, or butoxy.
In one aspect, $R^{4a2}$ is hydrogen.
In a further aspect, $R^5$ is hydrogen.
In one aspect, $R^6$ is hydrogen.
In a specific aspect, the compound is present as:

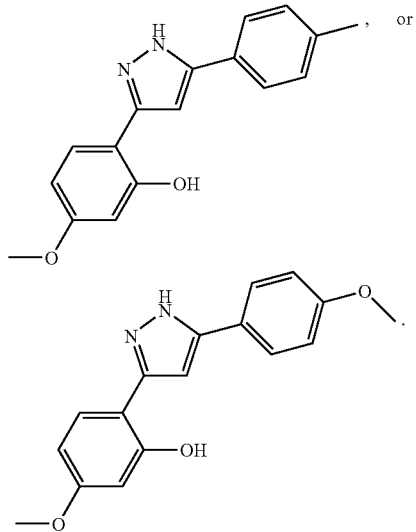

In one aspect, ---is present. In a further aspect, the compound has a structure represented by a formula:

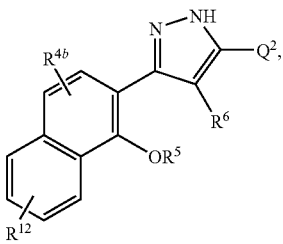

wherein $R^{12}$ comprises four substituents independently selected from hydrogen, hydroxyl, thiol, cyano, nitro, optionally substituted amino, azide, halide, and optionally substituted organic residue comprising from 1 to 4 carbons.

In a specific aspect, the compound is present as:

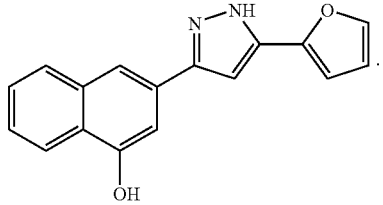

In a further aspect, a disclosed compound can be a Vitamin K. For example, the Vitamin K can have a structure represented by a formula:

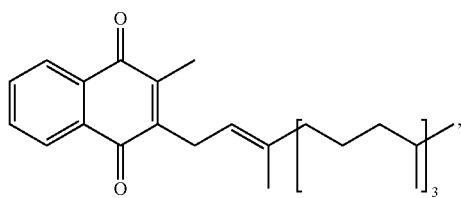

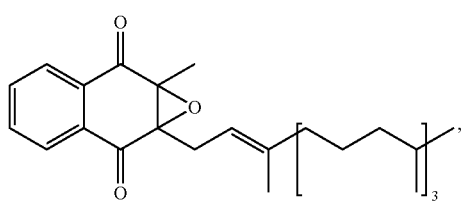

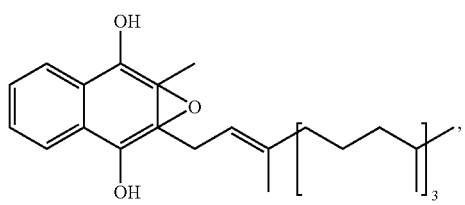

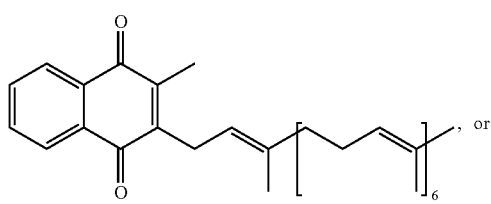

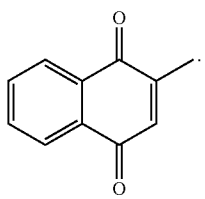

In one aspect, the Vitamin K is selected from: Vitamin $K_1$, Trans-vitamin $K_{1(20)}$-2,3-epoxide, Trans-vitamin K, Vitamin $K_2$; and Vitamin $K_3$.

D. HssRS SYSTEM ACTIVATING ACTIVITY

The utility of the compounds in accordance with the present invention as modulators of the HssRS system can be demonstrated by methodology known in the art or by disclosed methodology. For example, HssRS activating activity can be determined by the assays described hereinbelow.

In one aspect, a disclosed compound can be an effective activator of the HssRS system, thereby activating a heme efflux pump (HrtAB). In a further aspect, activating the heme efflux pump can result in modulating (e.g., decreasing) bacterial virulence.

In a further aspect, the compound can be selected from Table 1, which shows results from the Newman test, or Table 2, which shows results from the Stern test. Methods for obtaining the data shown in Tables 1 and 2 are described herein.

With reference to Table 1, "Luminescence" refers to the raw luminescence value obtained in a luminomter. "Control (82.5 nm)" refers to the luminescence value obtained from heme at 82.5 nM as a positive control in the same plate as the experimental. "% lum" is the percentage of luminescence induced by the compound as compared to the heme control in the same plate. "XylE 0.05" is the level of XylE induction exhibited upon exposure to 0.05 uM of the compound. "XylE 0.5" is the level of XylE induction exhibited upon exposure to 0.5 uM of the compound. "XylE 5.0" is the level of induction exhibited upon exposure to 5.0 uM of the compound. "XylE 50.0" is the level of induction exhibited upon exposure to 50.0 uM of the compound. "HssR dep" refers to whether or not the XylE inducing activity exhibited by the compound requires the response regulator HssR (+ indicates the XylE inducing activity does require the response regulator HssR; – indicates the activity does not). "Heme adapt" refers to whether or not the compound induces heme adaptation in the tested organism (+ indicates the compound induces heme adaptation; – indicates the compound does not). All of these assays are described in the application. In order to be selected as a candidate lead compound, a compound must exhibit at least 100% luminescence compared to the positive control, exhibit dose dependent increase in XylE activity, require HssR for activity, and cause the organism to adapt to heme toxicity. "N/T" indicates the test was not performed.

TABLE 1
| | NEWMAN | | | | | | | |
|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
|  | 1794 | 480 | 373.75% | 0.09 | 0.07 | 0.08 | 0.2 | N/T | N/T |
| 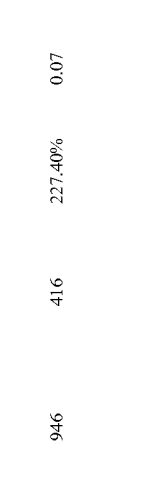 | 946 | 416 | 227.40% | 0.07 | 0.3 | 0.09 | 0.3 | N/T | N/T |
| 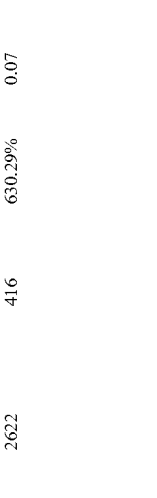 | 2622 | 416 | 630.29% | 0.07 | 0.06 | 0.2 | 1000 | + | + |
|  | 757 | 285 | 265.61% | 0.06 | 0.05 | 0.7 | 200 | + | + |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 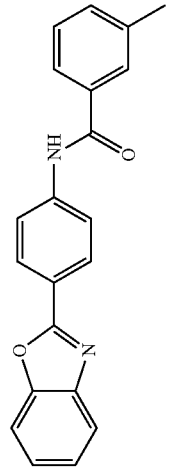 | 837 | 285 | 293.68% | 0.07 | 0.09 | 0.08 | 0.2 | N/T | N/T |
| 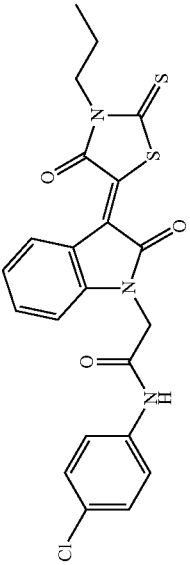 | 1600 | 635 | 251.97% | 1 | 0.06 | 0.07 | 0.02 | − | N/T |
| 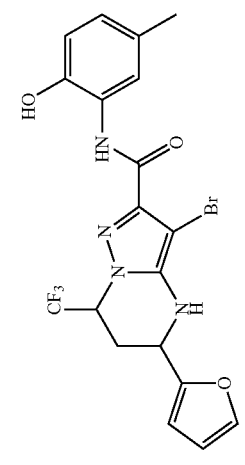 | 1949 | 635 | 306.93% | 0.05 | 0.06 | 5 | 3 | + | + |
| 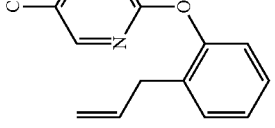 | 1474 | 5355 | 27.53% | 0.08 | 0.02 | 0.07 | 0.09 | N/T | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 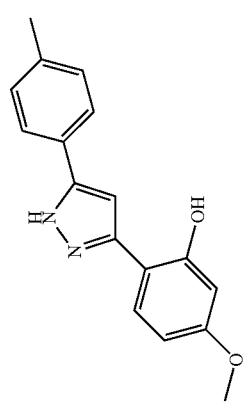 | 1122 | 624 | 179.81% | 0.08 | 0.02 | 0.07 | 0.09 | + | + |
| 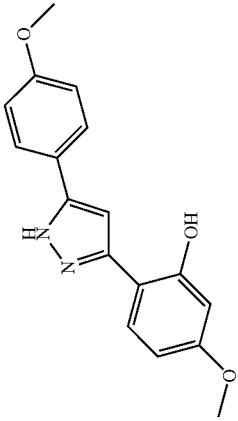 | 1482 | 624 | 237.50% | 0.06 | 0.02 | 0.7 | 4 | + | + |
| 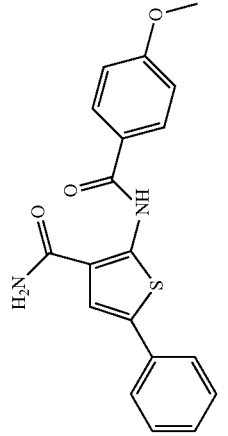 | 1781 | 730 | 243.97% | 0.07 | 0.09 | 4 | 6 | + | + |
| 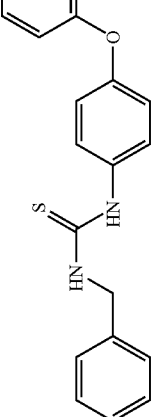 | 1570 | 434 | 361.75% | 0.06 | 0.05 | 0.2 | 1 | + | + |

TABLE 1-continued
| | NEWMAN | | | | | | | |
|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 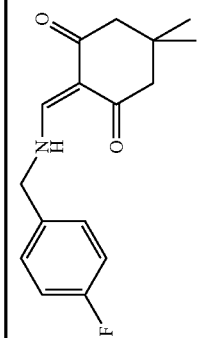 | 1003 | 838 | 119.69% | 0.07 | 0.09 | 0.9 | 0.06 | N/T | N/T |
| 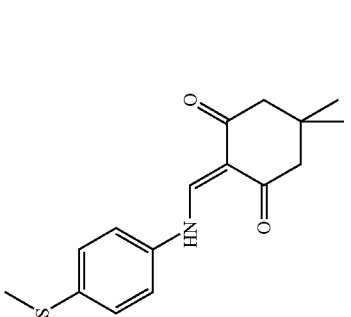 | 1347 | 838 | 160.74% | 0.04 | 0.05 | 0.01 | 1 | N/T | N/T |
| 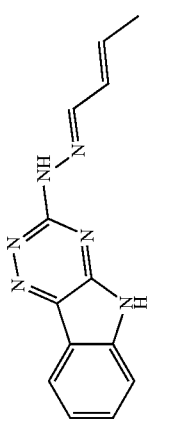 | 1696 | 838 | 202.39% | 0.04 | 0.06 | 0.1 | 1 | N/T | N/T |
| 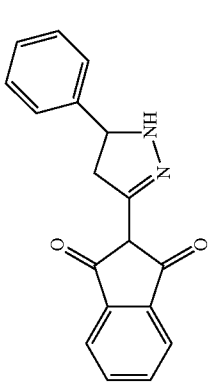 | 2680 | 3282 | 81.66% | 0.05 | 0.06 | 0.1 | 0.8 | N/T | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 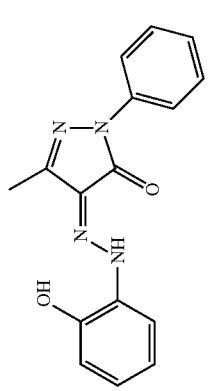 | 1848 | 3064 | 60.31% | 0.07 | 0.05 | 0.2 | 1 | - | N/T |
| 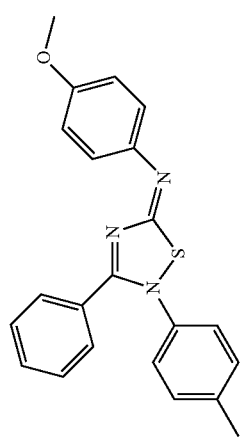 | 757 | 285 | 265.61% | 0.02 | 0.04 | 0 | 0 | N/T | N/T |
| 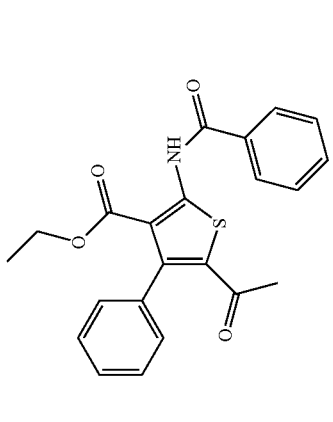 | 312 | 285 | 109.47% | 0.03 | 1 | 0.3 | 0.08 | - | N/T |
| 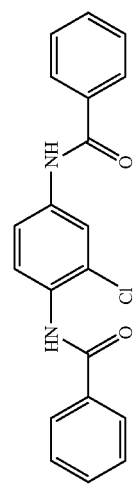 | 291 | 285 | 102.11% | 0.06 | 0.05 | 0.07 | 0.02 | N/T | N/T |

TABLE 1-continued
| Compound | NEWMAN Luminescence | Control (82.5 nm) | % Lumi | XylE (0.05) | XylE (0.5) | XylE (5.0) | XylE (50.0) | HssR Dep | Heme Adapt |
|---|---|---|---|---|---|---|---|---|---|
|  | 837 | 285 | 293.68% | 0.09 | 0.7 | 1 | 0.09 | + | + |
| 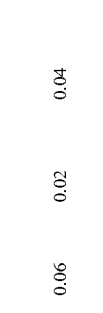 | 576 | 422 | 136.49% | 0.09 | 0.06 | 0.02 | 0.04 | N/T | N/T |
|  | 757 | 285 | 265.61% | 0.04 | 0.1 | 0.7 | 0.05 | + | + |
|  | 794 | 366 | 216.94% | 0.02 | 0.09 | 0.1 | 0.02 | N/T | N/T |
|  | 507 | 366 | 138.52% | 0.07 | 0.04 | 0.2 | 0.05 | N/T | N/T |

TABLE 1-continued

| Compound | NEWMAN | | | | | | | | |
|---|---|---|---|---|---|---|---|---|---|
| | Luminescence | Control (82.5 nm) | % Lumi | XylE (0.05) | XylE (0.5) | XylE (5.0) | XylE (50.0) | HssR Dep | Heme Adapt |
| 4-Br-phenyl furan acylhydrazone benzodioxine | 485 | 366 | 132.51% | 0.02 | 0.08 | 0.7 | 0.2 | + | + |
| 3-CF₃-phenyl furan acylhydrazone benzodioxine | 558 | 366 | 152.46% | 0.07 | 0 | 0.6 | 0.09 | + | + |
| 5-Br-2-OH-phenyl thiosemicarbazone m-tolyl | 589 | 366 | 160.93% | 0.09 | 0.2 | 0 | 0 | N/T | N/T |
| 2-Cl-phenyl bis-thiophene-2-carboxamide | 406 | 366 | 110.93% | 0.05 | 0.05 | 0.9 | 0.06 | – | N/T |

TABLE 1-continued
| | NEWMAN | | | | | | | |
|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 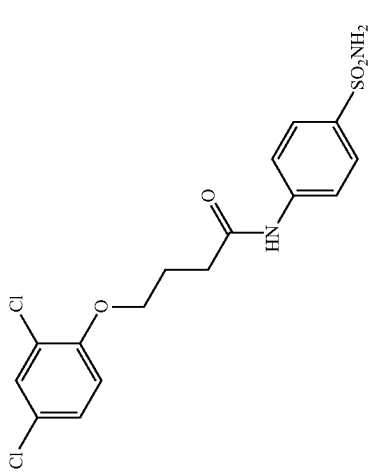 | 325 | 712 | 45.65% | 0.03 | 0.05 | 3 | 0 | N/T | N/T |
| | 309 | 336 | 91.96% | 0.05 | 0.08 | 0.08 | 0.06 | N/T | N/T |
| 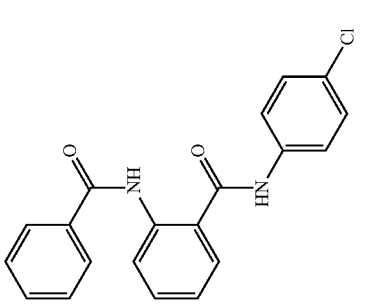 | 534 | 422 | 126.54% | 0 | 0 | 1 | 1 | N/T | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
|  | 576 | 422 | 136.49% | 1 | 0.05 | 0.02 | 1 | N/T | N/T |
| 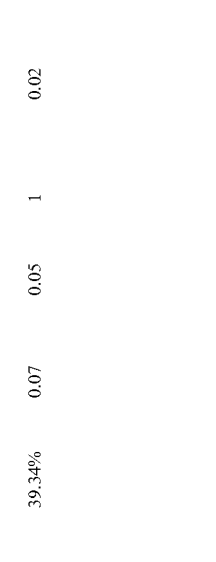 | 166 | 422 | 39.34% | 0.07 | 0.05 | 1 | 0.02 | N/T | N/T |
| 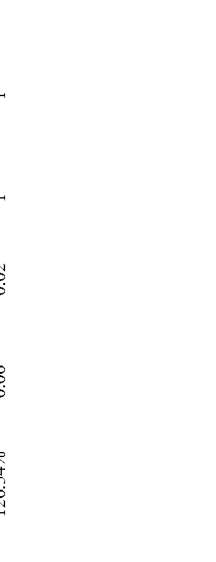 | 534 | 422 | 126.54% | 0.06 | 0.02 | 1 | 1 | N/T | N/T |
|  | 618 | 422 | 146.45 | 0.02 | 0.07 | 0.5 | 0.1 | N/T | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
|  | 586 | 326 | 179.75% | 1 | 0.03 | 0 | 0.03 | N/T | N/T |
| 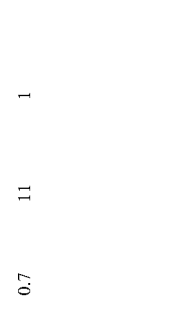 | 1949 | 635 | 306.93% | 0.07 | 0.7 | 11 | 1 | N/T | N/T |
|  | 1794 | 480 | 373.75% | 0.1 | 0.7 | 0.8 | 0.8 | N/T | N/T |
|  | 678 | 635 | 106.77% | 0.09 | 4 | 5 | 6 | N/T | N/T |

TABLE 1-continued

| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| ![structure] | 946 | 416 | 227.40% | 0.08 | 0.8 | 0.9 | 2 | + | + |
| ![structure] | 419 | 416 | 100.72% | 0.09 | 0.8 | 0.9 | 1 | + | + |
| ![structure] | 2622 | 416 | 630.29% | 0.4 | 0.07 | 12 | 5 | + | + |
| ![structure] | 808 | 635 | 127.24% | 0.09 | 0.2 | 0.2 | 0.3 | N/T | N/T |

TABLE 1-continued

| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| (structure) | 98 | 635 | 15.43% | 0.02 | 0.04 | 0.05 | 1 | + | + |
| (structure) | 2805 | 322 | 871.12% | 0.02 | 0.05 | 1 | 1 | N/T | N/T |
| (structure) | 3086 | 195 | 1582.56% | 0 | 1 | 1 | 0.7 | N/T | N/T |
| (structure) | 5542 | 266 | 2083.46% | 1 | 0.03 | 0.04 | 0.3 | N/T | N/T |
| (structure) | 4946 | 266 | 1859.40% | 0.04 | 1 | 1 | 0.02 | N/T | N/T |

TABLE 1-continued

| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| *(structure: thiourea with CCl₃, octanoyl amide, 2-hydroxyphenyl)* | 2766 | 195 | 1418.46% | 0.5 | 0.2 | 0.04 | 0.03 | N/T | N/T |
| *(structure: 3-methyl-2-phenylquinoline-4-carboxamide with 2-CF₃-phenyl)* | 2424 | 146 | 1660.27% | 0.5 | 0.7 | 0.03 | 0.02 | N/T | N/T |
| *(structure: fluorene bis-sulfonamide with p-tolyl groups)* | 7328 | 274 | 2674.45% | 1 | 1 | 15 | 14 | + | + |
| *(structure: pyrazolo-indeno-quinolinone with 4-nitrophenyl, OH, phenyl)* | 2608 | 83 | 3142.17% | 0.4 | 1 | 0.3 | 1 | N/T | N/T |

TABLE 1-continued
| | | NEWMAN | | | | | | |
|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| | 4302 | 339 | 1269.03% | 1 | 1 | 0.5 | 0.2 | — | N/T |
| | 2830 | 798 | 354.64% | 1 | 0.5 | 0.8 | 5 | — | N/T |
| | 2374 | 82 | 2895.12% | 8 | 2 | 1 | 1 | N/T | N/T |
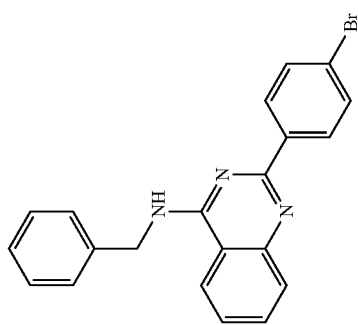
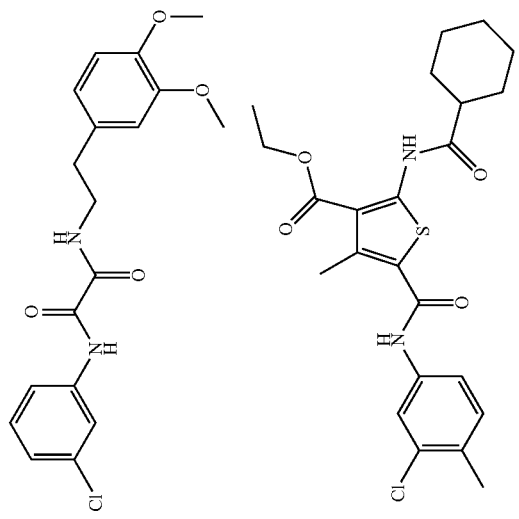

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 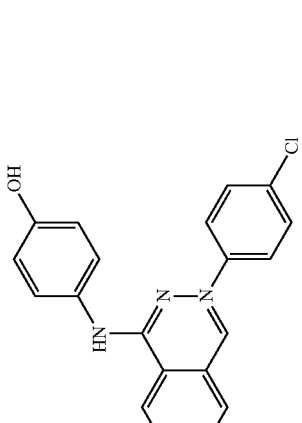 | 2098 | 85 | 2468.24% | 0.5 | 6 | 1 | 0.6 | N/T | N/T |
| 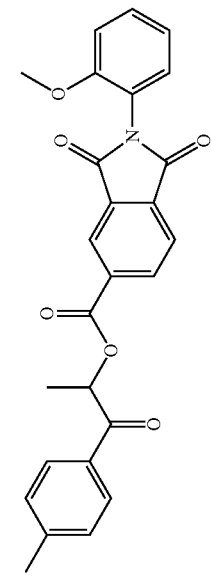 | 3189 | 294 | 1084.69% | 1 | 0.6 | 0.7 | 1 | N/T | N/T |
| 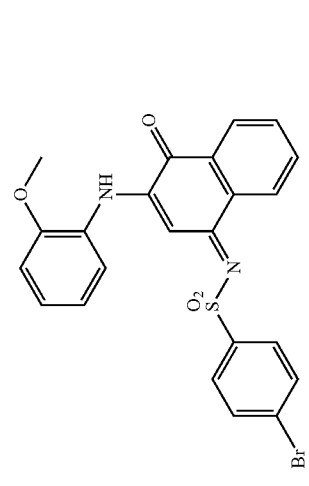 | 2270 | 445 | 510.11% | 1 | 1 | 1 | 1 | + | + |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 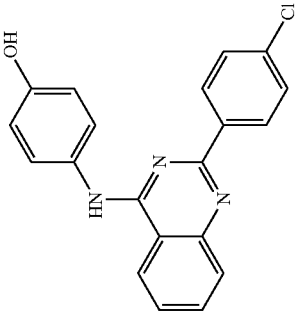 | 3096 | 185 | 1673.51% | 1 | 1 | 1 | 1 | N/T | N/T |
| | 2146 | 214 | 1002.80% | 1 | 1 | 9 | 1 | N/T | N/T |
| 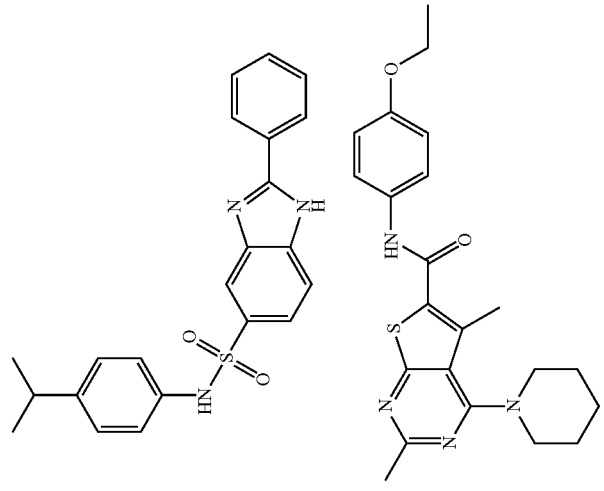 | 2277 | 211 | 1079.15% | 1 | 0.07 | 1 | 1 | N/T | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 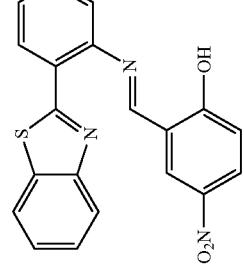 | 2904 | 461 | 629.93% | 1 | 50 | 1 | 1 | N/T | N/T |
| 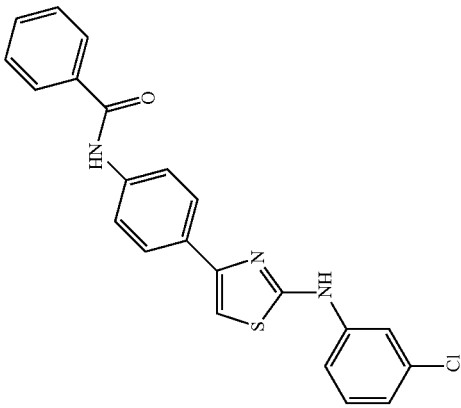 | 3586 | 80 | 4482.50% | 1 | 0.07 | 1 | 0.08 | N/T | N/T |
| 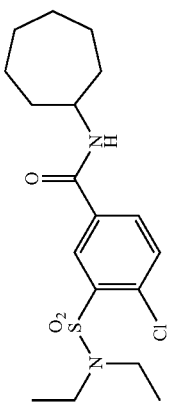 | 2080 | 274 | 759.12% | 1 | 1 | 1 | 0.05 | N/T | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
|  | 2301 | 211 | 1090.52% | 1 | 1 | 1 | 7 | N/T | N/T |
| 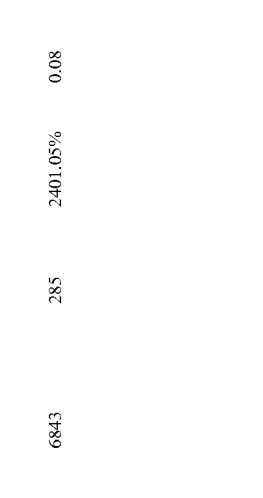 | 6843 | 285 | 2401.05% | 0.08 | 1 | 50 | 1 | + | N/T |
| 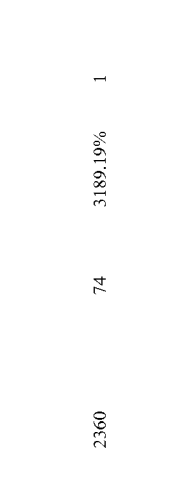 | 2360 | 74 | 3189.19% | 1 | 1 | 1 | 3 | − | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 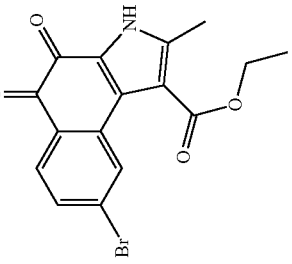 | 2896 | 1205 | 240.33% | 1 | 1 | 0.09 | 0.3 | N/T | N/T |
| 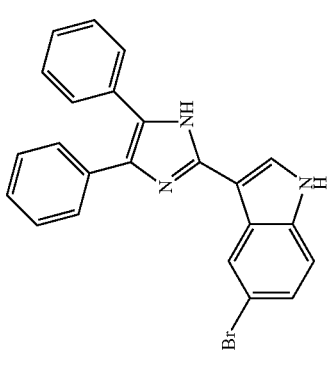 | 2549 | 64 | 3982.81% | 0.4 | 2 | 1 | 1 | N/T | N/T |
| 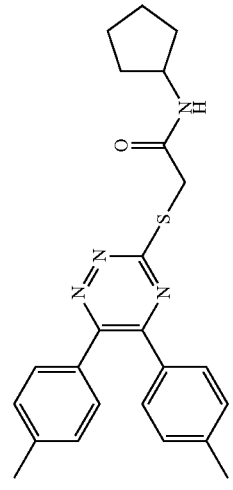 | 1658 | 194 | 854.64% | N/A | 1 | 0.5 | 0.04 | — | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
|  | 1642 | 365 | 449.86% | N/A | 0 | 0.05 | 0.09 | N/T | N/T |
| 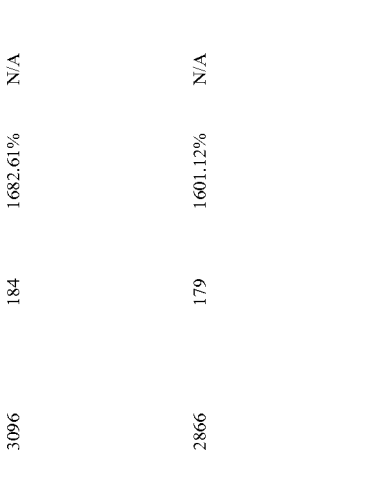 | 3096 | 184 | 1682.61% | N/A | 0.09 | 0.03 | 0.02 | N/T | N/T |
|  | 2866 | 179 | 1601.12% | N/A | 0.03 | 0.04 | 0.06 | N/T | N/T |

TABLE 1-continued

| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| [structure: 2-fluoro-N-(4-trifluoromethylphenyl)-5-(N-(4-fluorobenzyl)sulfamoyl)benzamide] | 1710 | 347 | 492.80% | N/A | 0 | 0.03 | 0.03 | N/T | N/T |
| [structure: bis-coumarin with 5-nitrofuran] | 1939 | 347 | 558.79% | N/A | 0.02 | 0.07 | 0 | N/T | N/T |
| [structure: N-(benzo[d][1,3]dioxol-5-yl)-2-(p-tolyl)quinazolin-4-amine] | 2101 | 90 | 2334.44% | N/A | 0.04 | 0 | 0 | N/T | N/T |

TABLE 1-continued

| Compound | NEWMAN | | | | | | | |
|---|---|---|---|---|---|---|---|---|
| | Luminescence | Control (82.5 nm) | % Lumi | XylE (0.05) | XylE (0.5) | XylE (5.0) | XylE (50.0) | HssR Dep | Heme Adapt |
| (structure) | 3115 | 59 | 5279.66% | N/A | 1 | 0 | 0 | N/T | N/T |
| (structure) | 1995 | 283 | 704.95% | N/A | 0.04 | 0.08 | 0.05 | N/T | N/T |
| (structure) | 1765 | 512 | 344.73% | N/A | 0.1 | 0.6 | 0 | N/T | N/T |

TABLE 1-continued
| | NEWMAN | | | | | | | |
|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 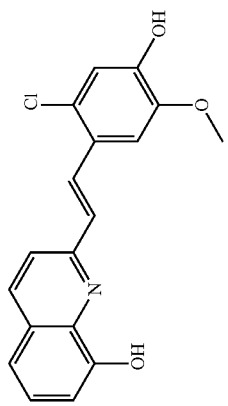 | 1722 | 323 | 533.13% | N/A | 1 | 0.5 | 0 | N/T | N/T |
| 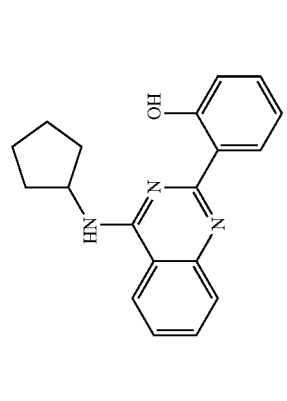 | 1637 | 277 | 590.97% | N/A | 0.09 | 0.02 | 0 | N/T | N/T |
| 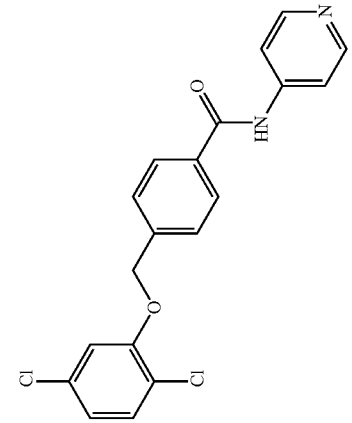 | 1845 | 309 | 597.09% | N/A | 1 | 0.4 | 1 | N/T | N/T |

TABLE 1-continued

| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| (structure) | 1774 | 427 | 415.46% | N/A | 0.01 | 0.09 | 0.01 | N/T | N/T |
| (structure) | 1589 | 355 | 477.61% | N/A | 0.09 | 0 | 1 | N/T | N/T |
| (structure) | 1822 | 152 | 1198.68% | N/A | 0.03 | 0.08 | 11 | + | N/A |
| (structure) | 1741 | 160 | 1088.13% | N/A | 0.01 | 0.03 | 0.04 | N/T | N/T |

TABLE 1-continued

| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| | 1714 | 354 | 484.18% | N/A | 0.03 | 0.02 | 0.8 | N/T | N/T |
| | 2763 | 158 | 1748.73% | N/A | 0 | 0.2 | 0.4 | N/T | N/T |
| | 1630 | 470 | 346.81% | N/A | 0.06 | 0 | 0.9 | N/T | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 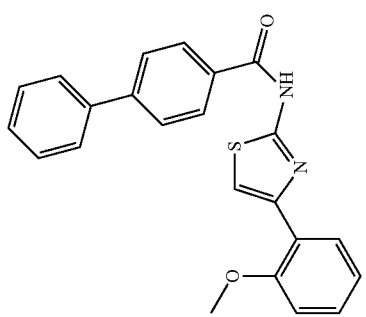 | 1704 | 118 | 1444.07% | N/A | 0.05 | 1 | 1 | N/T | N/T |
| 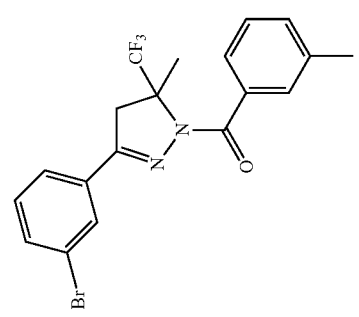 | 1683 | 294 | 572.45% | N/A | 0.04 | 0.08 | 0.1 | N/T | N/T |
| 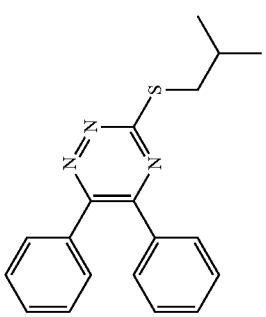 | 1706 | 445 | 383.37% | N/A | 0.04 | 0.07 | 1 | + | N/A |

TABLE 1-continued

| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| ![structure] | 1574 | 445 | 353.71% | N/A | 0.03 | 0.06 | 0.05 | N/T | N/T |
| ![structure] | 1747 | 624 | 279.97% | N/A | 4 | 4 | 7 | — | N/T |
| ![structure] | 1850 | 274 | 675.18% | N/A | 0.02 | 0 | 0.03 | N/T | N/T |
| ![structure] | 1678 | 798 | 210.28% | N/A | 0.05 | 0.03 | 0.04 | N/T | N/T |

TABLE 1-continued

| Compound | NEWMAN Luminescence | Control (82.5 nm) | % Lumi | XylE (0.05) | XylE (0.5) | XylE (5.0) | XylE (50.0) | HssR Dep | Heme Adapt |
|---|---|---|---|---|---|---|---|---|---|
| [structure: phenyl-NH-C(O)-CH2-O-thiadiazole-morpholine] | 1594 | 771 | 206.74% | N/A | 0.05 | 0.02 | 0.03 | N/T | N/T |
| [structure: di-tert-butyl benzoxazoline with nitrophenol] | 1805 | 86 | 2098.84% | N/A | 0.04 | 0 | 0.04 | N/T | N/T |
| [structure: chloro-nitro-benzamide with methyl-phenyl-benzoxazole] | 1912 | 70 | 2731.43% | N/A | 0.06 | 0.1 | 0.5 | N/T | N/T |
| [structure: methoxybenzamide-phenyl-ethylbenzoxazole] | 2392 | 69 | 3466.67% | N/A | 0.05 | 2 | 3 | (+) | N/A |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 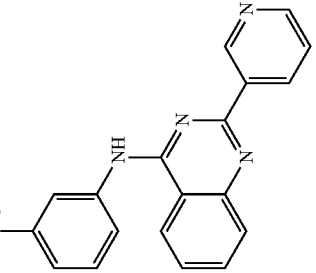 | 1616 | 75 | 2154.67% | N/A | 0.02 | 0.05 | 0.02 | N/T | N/T |
| 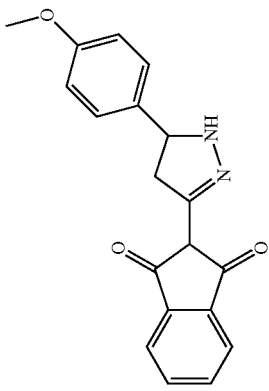 | 1888 | 88 | 1245.45% | N/A | 0.08 | 5 | 0.09 | N/T | N/T |
| 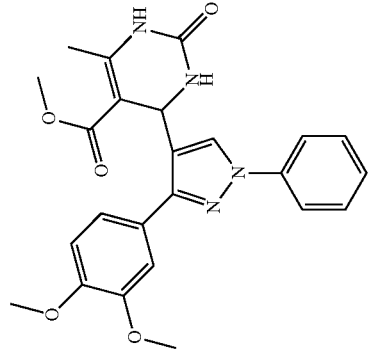 | 1854 | 214 | 866.36% | N/A | 0.04 | 0.03 | 0.05 | N/T | N/T |

TABLE 1-continued

| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| [structure: 5-((4-methylbenzylthio)methyl)-N-(4-fluorobenzyl)furan-2-carboxamide] | 1653 | 834 | 198.20% | N/A | 0 | 3 | 5 | + | N/A |
| [structure: N-(4-methylbenzyl)-5-((2-chlorobenzylthio)methyl)furan-2-carboxamide] | 1603 | 834 | 192.21% | N/A | 0.08 | 0.7 | 0.8 | N/T | N/T |

TABLE 1-continued
| | NEWMAN | | | | | | | | |
|---|---|---|---|---|---|---|---|---|---|
| Compound | Luminescence | Control (82.5 nm) | % Lumi | XylE (0.05) | XylE (0.5) | XylE (5.0) | XylE (50.0) | HssR Dep | Heme Adapt |
| 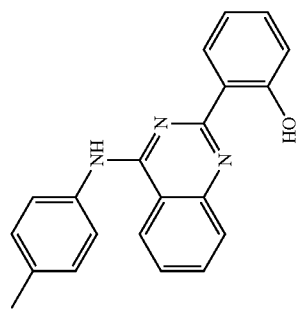 | 1922 | 534 | 359.93% | N/A | 0.04 | 0.1 | 0.08 | N/T | N/T |
| 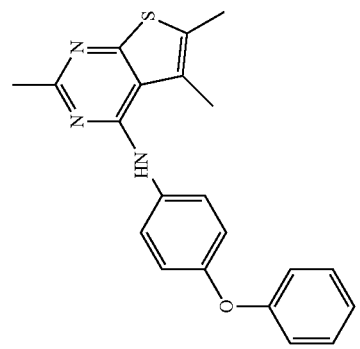 | 1627 | 107 | 1520.56% | N/A | 0.6 | 0.09 | 0 | – | N/T |

TABLE 2

| STERN | | | |
|---|---|---|---|
| Compound | HssR Dep | Heme Adapt | Toxicity |
| *3-(furan-2-yl)-5-(1-hydroxynaphthalen-2-yl)-1H-pyrazole* | − | − | + |
| *N-(1-(2,3-dihydrobenzo[b][1,4]dioxin-2-yl)ethyl)-1-phenylcyclopentanecarboxamide* | + | + | − |
| *2,3-dihydrobenzo[b][1,4]dioxine-2-carbohydrazide furan-bromophenyl* | + | + | − |
| *2,3-dihydrobenzo[b][1,4]dioxine-2-carbohydrazide furan-(trifluoromethyl)phenyl* | − | − | + |
| *fluorene bis-sulfonamide di-tolyl* | + | + | − |
| *naphthoquinone methoxyphenylamino bromophenylsulfonylimino* | + | + | − |

In a further aspect, an effective activator of the HssRS system can be a disclosed compound listed in Table 3.

TABLE 3

| Compound ID | Structural Formula |
| --- | --- |
| C3 | |
| C4 | |
| C7 | |
| C9 | |
| C10 | |
| C11 | |

TABLE 3-continued

| Compound ID | Structural Formula |
|---|---|
| C12 | |
| C21 | |
| C23 | |
| C26 | |
| C27 | |
| C41 | |
| C42 | |
| C45 | |

E. METHODS OF MAKING THE COMPOUNDS

Certain materials, compounds, compositions, and components disclosed herein can be obtained commercially (e.g., through libraries) or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

F. PHARMACEUTICAL COMPOSITIONS

In one aspect, the invention relates to pharmaceutical compositions comprising the disclosed compounds. For example, the compositions can comprise a heme sensor system activator, and/or one or more disclosed compounds, including napthol derivatives, hydroquinone derivatives, and vitamins and vitamin derivatives.

In a further aspect, a pharmaceutical composition comprises a therapeutically effective amount of at least one disclosed compound and a pharmaceutically acceptable carrier. In a further aspect, a pharmaceutical composition comprises a therapeutically effective amount of at least one product of a disclosed method and a pharmaceutically acceptable carrier. In a further aspect, a pharmaceutical composition comprising a therapeutically effective amount of at least one phenylethynylbenzamide derivative and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

An amount of a heme sensor system activator is expected to vary from about 0.1 milligram per kilogram of body weight per day (mg/kg/day) to about 100 mg/kg/day. Preferred amounts of a co-administered antimicrobial agent can vary by amounts known in the art, in so far as they relate to the antimicrobial agent selected.

The present invention is further directed to a method for the manufacture of a medicament for treating disorders associated with bacterial infections in mammals (e.g., humans) comprising combining a compound of the present invention with a pharmaceutically acceptable carrier or diluent.

Thus, in one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

The disclosed pharmaceutical compositions can further comprise other therapeutically active compounds, which are usually applied in the treatment of the above mentioned pathological conditions, as further discussed hereinbelow.

Thus, in one aspect, the invention also relates to methods of coadminstering to a mammal at least one disclosed compound and one or more other therapeutically active compounds, which are usually applied in the treatment of the above mentioned pathological conditions. For example, the disclosed methods can relate to coadministration of therapeutically effective amounts of one or more heme sensor system activators with one or more antimicrobial agents.

In a further aspect, the invention also relates to kits comprising at least one disclosed compound and one or more other therapeutically active compounds, which are usually applied in the treatment of the above mentioned pathological conditions. For example, the disclosed kits can comprise therapeutically effective amounts of one or more disclosed compound and one or more antimicrobial agents. The kits can be co-packaged, co-formulated, and/or co-delivered with the antimicrobial agents. For example, a drug manufacturer, a drug reseller, a physician, or a pharmacist can provide a disclosed kit for delivery to a patient.

In various aspects, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

It is understood that the disclosed compositions can be employed in the disclosed methods of using.

G. METHODS OF USING THE COMPOUNDS AND COMPOSITIONS

In one aspect, disclosed are methods for activating a heme sensor system in at least one bacterium comprising the step of contacting the at least one bacterium with an effective amount of a compound identified by a heme sensor system activator screen, thereby activating a heme efflux pump (HrtAB) in the at least one bacterium. In one aspect, the heme sensor system can be the HssRS system, as described hereinelsewhere.

1. Treatment Methods

Disclosed are methods for treating a bacterial infection in a mammal comprising the step of administering a therapeutically effective amount of a compound identified by a heme sensor system activator screen, thereby decreasing bacterial virulence in the mammal. In one aspect, activating the heme efflux pump (HrtAB) decreases bacterial virulence.

In one aspect, the heme sensor system activator screen comprises the steps described in various examples of assays described herein.

In one aspect, the bacterium is a gram-positive bacterium. In a further aspect, the bacterium is a gram-positive pathogen.

In one aspect, the bacterium is a gram-positive pathogen. For example, the bacterium can be selected from *Bacillus anthracis, Bacillus cereus, Listeria monocytogenes, Listeria innocua, Enterococcus faecalis, Staphylococcus aureus, Staphylococcus epidermidis, Staphylococcus haemolyticus, Staphylococcus saprophyticus*, and *Lactococcus lactis*.

In a further aspect, the step of contacting results in modulated bacterial virulence. For example, in one aspect, activating the heme sensor system decreases bacterial virulence. In a further aspect, activating the heme efflux pump (HrtAB) decreases bacterial virulence.

In one aspect, a disclosed method further comprises the step of administering a therapeutically effective amount of one or more antimicrobial agents.

In one aspect, disclosed are methods for treating a bacterial infection in a mammal comprising the step of co-administering a therapeutically effective amount of a heme sensor system activator and a therapeutically effective amount of one or more antimicrobial agents, thereby treating the infection in the mammal. For example, a heme sensor system activator can be a compound identified by a heme sensor system activator screen. In a further example, a heme sensor system activator can be a disclosed compound.

In one aspect, the antimicrobial agent to be co-administered with one or more disclosed compounds or compounds identified by a heme sensor system activator can be selected from one or more of Geldanamycin; Herbimycin; Carbacephem; Loracarbef; Ertapenem; Doripenem; Imipenem/Cilastatin; Meropenem; Cefadroxil; Cefazolin; Cefalotin; Cefalothin; Cefalexin; Cefaclor; Cefamandole; Cefoxitin; Cefprozil; Cefuroxime; Cefixime; Cefdinir; Cefditoren; Cefoperazone; Cefotaxime; Cefpodoxime; Ceftazidime; Ceftibuten; Ceftizoxime; Ceftriaxone; Cefepime; Ceftobiprole; Teicoplanin; Vancomycin; Macrolides; Azithromycin; Clarithromycin; Dirithromycin; Erythromycin; Roxithromycin; Troleandomycin; Telithromycin; Spectinomycin; Aztreonam; Amoxicillin; Ampicillin; Azlocillin; Carbenicillin; Cloxacillin; Dicloxacillin; Flucloxacillin; Mezlocillin; Meticillin; Nafcillin; Oxacillin; Penicillin; Piperacillin; Ticarcillin; Bacitracin; Colistin; Polymyxin B; Quinolones; Ciprofloxacin; Enoxacin; Gatifloxacin; Levofloxacin; Lomefloxacin; Moxifloxacin; Norfloxacin; Ofloxacin; Trovafloxacin; Mafenide; Prontosil; Sulfacetamide; Sulfamethizole; Sulfanilimide; Sulfasalazine; Sulfisoxazole; Trimethoprim; Trimethoprim-Sulfamethoxazole (Co-trimoxazole) (TMP-SMX); Demeclocycline; Doxycycline; Minocycline; Oxytetracycline; Tetracycline; Arsphenamine; Chloramphenicol; Clindamycin; Lincomycin; Ethambutol; Fosfomycin; Fusidic acid; Furazolidone; Isoniazid; Linezolid; Metronidazole; Mupirocin; Nitrofurantoin; Platensimycin; Pyrazinamide; Quinupristin/Dalfopristin; Rifampin or Rifampicin; and Tinidazole.

Also disclosed are kits comprising a therapeutically effective amount of a heme sensor system activator and a therapeutically effective amount of one or more antimicrobial agents. For example, a kit can comprise one or more heme sensor system activators and one or more antimicrobial agents. In a further example, one or more heme sensor system activators and one or more antimicrobial agents can be co-formulated.

In a further aspect, a kit composition can be co-packaged. For example, a co-package can comprise a heme sensor system activator and one or more antimicrobial agents.

In one aspect, the antimicrobial agent can be specific for gram-positive bacteria.

In another aspect, the antimicrobial agent can be selected from one or more of Geldanamycin; Herbimycin; Carbacephem; Loracarbef; Ertapenem; Doripenem; Imipenem/Cilastatin; Meropenem; Cefadroxil; Cefazolin; Cefalotin; Cefalothin; Cefalexin; Cefaclor; Cefamandole; Cefoxitin; Cefprozil; Cefuroxime; Cefixime; Cefdinir; Cefditoren; Cefoperazone; Cefotaxime; Cefpodoxime; Ceftazidime; Ceftibuten; Ceftizoxime; Ceftriaxone; Cefepime; Ceftobiprole; Teicoplanin; Vancomycin; Macrolides; Azithromycin; Clarithromycin; Dirithromycin; Erythromycin; Roxithromycin; Troleandomycin; Telithromycin; Spectinomycin; Aztreonam; Amoxicillin; Ampicillin; Azlocillin; Carbenicillin; Cloxacillin; Dicloxacillin; Flucloxacillin; Mezlocillin; Meticillin; Nafcillin; Oxacillin; Penicillin; Piperacillin; Ticarcillin; Bacitracin; Colistin; Polymyxin B; Quinolones; Ciprofloxacin; Enoxacin; Gatifloxacin; Levofloxacin; Lomefloxacin; Moxifloxacin; Norfloxacin; Ofloxacin; Trovafloxacin; Mafenide; Prontosil; Sulfacetamide; Sulfamethizole; Sulfanilimide; Sulfasalazine; Sulfisoxazole; Trimethoprim; Trimethoprim-Sulfamethoxazole (Co-trimoxazole) (TMP-SMX); Demeclocycline; Doxycycline; Minocycline; Oxytetracycline; Tetracycline; Arsphenamine; Chloramphenicol; Clindamycin; Lincomycin; Ethambutol; Fosfomycin; Fusidic acid; Furazolidone; Isoniazid; Linezolid; Metronidazole; Mupirocin; Nitrofurantoin; Platensimycin; Pyrazinamide; Quinupristin/Dalfopristin; Rifampin or Rifampicin; and Tinidazole.

The compounds disclosed herein are useful for treating, preventing, ameliorating, controlling or reducing the risk of a variety of disorders related to bacterial virulence. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

2. Manufacture of a Medicament

Also provided is a method for the manufacture of a medicament for treatment of a disorder in a subject, comprising the step of mixing together a heme sensor system activator and a pharmaceutically acceptable carrier, as discussed herein elsewhere.

3. Use of Compounds

Also provided are uses of the disclosed compounds. For example, disclosed is the use of a heme sensor system activator. In one aspect, the heme sensor system activator can be a disclosed compound. In a further aspect, the heme sensor system activator can be a compound identified by a screening method disclosed herein. For example, the heme sensor system activator can be a compound identified from a library, as defined hereinelsewhere.

In one aspect, the use can be for the treatment of a disorder in a subject, e.g. a mammal. In one aspect, the use is characterized in that the mammal is a human. In one aspect, the use relates to a treatment of a disorder in a mammal.

In one aspect, the use is characterized in that the disorder is a bacterial infection.

4. Screening Assay

Disclosed are methods for identifying a heme sensor system activator comprising the steps of: contacting a cell with a candidate agent, wherein the cell comprises a nucleic acid comprising a reporter element operably linked to an htrAB expression control sequence; and detecting gene expression of the reporter element, wherein an increase in gene expression of the reporter element compared to a control is an indication that the candidate agent is a heme sensor system activator.

In one aspect, the htrAB expression control sequence is a direct repeat sequence in the hrtAB promoter. In a further aspect, the htrAB expression control sequence comprises the nucleic acid sequence SEQ ID NO: 1 (GTTCATATTNNGT-TCATATT).

In one aspect, the reporter element is a fluorochrome, luciferase, or substrate for a luciferase. In a further aspect, the reporter element encodes fatty acid reductase (LuxCDE). In one aspect, the reporter element comprises luxCDABE. In a further aspect, detecting is performed by luminescence.

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods. In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effect on the activity of HssRS should be employed whenever possible.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having a disclosed activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions, such as those disclosed herein.

Candidate agents encompass numerous chemical classes, but are most often organic molecules, e.g., small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, for example, at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In a further embodiment, candidate agents are peptides.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

5. Subjects

The subject of the herein disclosed methods can be a mammal, for example, a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In one aspect, the subject has been identified with a need for treatment of a bacterial infection prior to the administration step. In a further aspect, the subject has been diagnosed with the bacterial infection prior to the administration step.

H. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Luminescence-Based Assay to Monitor HssRS-Dependent hrtAB Expression

A hrtAB-driven expression system was created in the pXen vector system (Xenogen) (Francis, K. P., D. Joh, C. Bellinger-Kawahara, M. J. Hawkinson, T. F. Purchio, and P. R. Contag. 2000. Monitoring bioluminescent *Staphylococcus aureus* infections in living mice using a novel luxABCDE construct. Infect Immun 68:3594-3600). This vector contains a promoterless luxCDABE operon from Photorabdus luminescens which produces blue green light when expressed. The luxCDABE encodes for a fatty acid reductase (LuxCDE) that produces a long chain fatty aldehyde which, when combined with cellular flavin mononucleotide, is oxidized by a luciferase (LuxAB) to produce light. Therefore, this system is useful in that it bypasses the need for substrate addition and is capable of generating light in the absence of any added reagents. Furthermore, the luminescent signal produced by the combined activities of LuxAB and LuxCDE is of sufficient intensity to be visualized in unmanipulated intact bacteria.

To establish an assay that measures HssRS-dependent expression of luxCDABE, the promoter for hrtAB upstream of luxCDABE was cloned and transformed this vector (phrtABlux) into wildtype and ΔhssR *S. aureus*. A promoterless vector (plux) and a plasmid containing luxCDABE under the control of a constitutive promoter (psrtAlux) (Mazmanian, S. K., G. Liu, H. Ton-That, and O. Schneewind. 1999. *"Staphylococcus aureus* sortase, an enzyme that anchors surface proteins to the cell wall." Science 285:760-763) were included as negative and positive controls, respectively. Initially, wildtype *S. aureus* harboring either plux, phrtABlux, or psrtAlux were plated on solid medium that either lacked heme or contained 4 µM heme. Only wildtype *S. aureus* containing psrtAlux produced light on solid media regardless of the presence or absence of heme. In contrast, *S. aureus* containing phrtABlux generated light exclusively upon heme exposure. Light was not produced by bacteria containing plux in either condition.

To adapt this system for a HTS to measure ligand recognition by HssRS, luminescence of wildtype and ΔhssR harboring the above listed plasmids in liquid media with or without heme was measured. These experiments demonstrated robust luminescence of *S. aureus* wildtype containing phrtABlux exclusively upon exposure to heme. Furthermore, this luminescence is dependent on HssRS as ΔhssR containing phrtABlux did not produce light in the presence of heme. Taken together, these experiments establish a whole cell "mix-and-bind" assay that can identify small molecule modifiers of HssRS. This screen, in some aspects, can identify molecules that can be used as molecular probes in structure-function analyses to determine the mechanism by which *S. aureus* sense host heme.

2. Assay for Identifying Molecular Activators of HssRS

Upon *staphylococcal* exposure to heme, HssRS senses heme and activates expression of hrtAB. This process can be measured using a reporter assay that employs a vector encoding the light-producing luxCDABE operon under the control of the hrtAB promoter. This assay results in whole cell luminescence upon HssRS-dependent activation of hrtAB, forming the foundation for the development of an assay suitable for high-throughput screens for small molecule activators of HssRS.

To develop an automated HTS format, *S. aureus* wildtype and ΔhssR harboring reporter constructs (psrtAlux, phrtAlux, plux) can be grown for 15 hours at 37° C. in tryptic soy broth (TSB) containing 10 µg/ml chloramphenicol. The addition of chloramphenicol is useful to ensure that the *staphylococci* propagate the reporter plasmid upon cell division. Following growth, bacterial cultures can be normalized and $2 \times 10^7$ cells (approximately 2 µl) can be added to individual wells of black walled, clear bottomed, 96-well plates. In advance of this inoculation, each well can contain 150 µl of TSB supplemented with 10 µg/ml chloramphenicol with or without heme. Plates can be incubated at 37° C. and luminescence will be measured using a luminometer at 20 minute intervals (the approximate doubling time of *S. aureus* under these growth conditions) for 9 hours. Concurrently, bacterial growth will be monitored using optical density as a measure at 600 nm (O.D.600). For this purpose, one can use one of Two Hamamatsu FDSS (Functional Drug Screening System) kinetic imaging plate readers that are available from commercial suppliers and in The Molecular Recognition and Screening Facility at Vanderbilt University. These instruments have integrated liquid handling and are capable of simultaneously making liquid additions to each well of either 384- or 96-well microplates as well as enabling multiple liquid additions to a test plate during the course of an experiment. The instruments acquire kinetic data from all wells of a microtiter plate simultaneously at rates of up to 10 Hz. These instruments are useful for acquiring nearly simultaneous luminescence and optical density readings, which can, in some aspects, virtually eliminate downtime between measurements. Luminescence per well can be normalized to the corresponding optical density to account for any confounding effects of altered growth kinetics. To evaluate the effect of DMSO on luminescence, this assay can be performed in the presence of concentrations of DMSO ranging from 0.1% to 1.0%.

To determine the sensitivity of this assay, *S. aureus* containing phrtABlux can be exposed to increasing concentrations of heme to determine the dynamic range of heme required to activate hrtAB. Preliminary results reveal a 100-fold increase in luminescence upon exposure of *S. aureus* to 3 µM heme. Using this concentration as a guide, concentrations of heme can be added ranging from about 30 µM to about 30 µM. Concentrations of heme above 30 µM are insoluble in solution and hence need not be evaluated. These experiments can be repeated using GaPPIX and MnPPIX as pharmacologically active standards to establish dose response across a range of activators as well as concentrations. These experiments can inform a user as to the optimal concentration of ligand necessary to activate hrtAB in this assay, and establish a dose response curve for heme-mediated luminescence.

To determine the signal to background ratio in this assay, parallel plates can be run as above using both wildtype harboring plux, and ΔhssR harboring phrtABlux. Considering that preliminary results suggest that heme-exposed wildtype harboring phrtABlux produces a 100-fold increase in luminescence over both of these negative control strains, it can be predicted that a user can establish an assay with a signal to background ratio that exceeds 50.

Optimization of this assay can be performed at 37° C.; however *S. aureus* is capable of growth at temperatures ranging from about 24° C. to about 45° C. In addition, the luxCDABE system used here is capable of light production across a similar temperature range, suggesting that the assay system can tolerate a wide variety of temperature conditions. To determine the temperatures at which the proposed screen can be performed, a user can conduct the 96-well plate based assay described above at 24° C., 30° C., 37° C., and 45° C. In one aspect, a user can find HssRS-mediated heme-dependent activation of hrtAB at room temperature as this can allow the user to perform subsequent HTS without the need for temperature control. It is understood that performing these assays at room temperature will slow the doubling time of S. aureus by approximately half, therefore readouts can be taken at extended timepoints to accommodate this growth change.

To establish the reproducibility of this assay, the user can measure luminescence from wildtype harboring phrtABlux in a 96-well plate-based assay where every other well is treated with the maximum effective dose of heme as determined above. The assay can be performed in triplicate on triplicate days allowing the user to determine well-to-well, plate-to-plate, and day-to-day variation. The user can use these data to measure the mean luminescence from heme treated and untreated samples for determination of the coefficient of variation. The system can be optimized to achieve a coefficient of variation below 10% which will be expressed individually as [100×mean of the population/standard deviation] or as a statistical parameter Z' which has an acceptable lower limit of 0.5. Z' can be calculated using the following formula:

$$1 - \frac{\left[\begin{array}{c}(3\times(\text{standard deviation of the positive control})+\\(3\times(\text{standard deviation of the negative control})\end{array}\right]}{(\text{mean of the positive control}) - (\text{mean of the negative control})}$$

The reagents used in this assay are TSB, chloramphenicol, and heme. These are common, commercially available chemicals. In addition, S. aureus is a clonal organism and a single strain of S. aureus (wildtype or isogenic ΔhssR mutant) can be used in each assay.

It should be appreciated that that compounds which kill S. aureus can lead to a decrease in optical density and commensurate decrease in luminescence produced from the constitutively active psrtAlux vector. Therefore, by including wildtype containing psrtAlux in these analyses, and incorporating O.D.600 measurements at all timepoints, a user can perform a parallel screen for small molecules that inhibit *staphylococcal* growth independent of the HssRS/HrtAB systems.

3. HssRS-Activator Assay for High Throughput Screening of Small Molecule Modifiers The assay discussed hereinabove can be miniaturized to 384-well plates and an initial screen for small molecule modifiers of HssRS using several hundred commercially available compounds to obtain an initial evaluation of the applicability of the assay for HTS can be performed. For example, a 1,280 membered Library of Pharmacologically Active Compounds (LOPAC) from Sigma-Aldrich can be screened. The LOPAC library includes pure, standardized concentrations of compounds that represent several major target classes. To validate the assay, a user can dispense the LOPAC library into wells containing TSB-chloramphenicol, and inoculate each well with wildtype phrtABlux as described hereinabove. Wildtype bacteria harboring plux and ΔhssR bacteria harboring phrtABlux can be included as negative controls. As positive controls, the user can include wildtype psrtAlux and exposed wildtype phrtABlux to a maximally inducing concentration of heme.

Compounds that activate HssRS-driven hrtAB expression in the luciferase-based screen can be subjected to two separate counter screens to confirm these compounds as active hits. First, compounds of interest can be tested for their ability to activate expression of hrtAB in the XylE expression assay described hereinbelow. This is an in vitro assay that measures hrtAB-driven expression of the xylE reporter gene. The XylE-based reporter assay utilizes slightly more manipulations than the primary luciferase-based screen. The increased sensitivity of the XylE-based counter screen can allow for one to (i) demonstrate the reproducibility of positive hits across assays, (ii) perform rigorous dose-ranging experiments, and (iii) eliminate false positives that non-specifically activate luciferase expression. It should be appreciated that a shortcoming of this counter screen is that it measures reporter gene expression, which is a similar activity as that measured in the primary assay. To address this shortcoming, compounds that are positive in both XylE- and luciferase-based assays can be subjected to a second counter screen as described hereinbelow.

To measure the effect of compounds on HssRS activation using an assay that does not measure reporter expression, a second counter screen can be employed. This secondary counter screen can involve testing the compounds of interest for their ability to increase the resistance of wildtype S. aureus to heme-mediated toxicity. Upon sensing heme, HssRS increases the expression of hrtAB, in turn increasing the resistance of S. aureus to heme mediated toxicity. By extension, additional molecules recognized by HssRS leading to hrtAB activation can result in a similar increase in resistance to heme mediated toxicity. For this assay, bacteria can be grown for 15 hours in the presence of compounds of interest (using concentrations determined in the XylE assay), followed by subculture into TSB containing 10 μM heme. Compounds that increase the resistance of S. aureus to heme-mediated toxicity can be selected for further studies. S. aureus strains unable to adapt to heme mediated toxicity (ΔhssR) can be included as a negative control. As a positive control, wildtype S. aureus can be exposed to subinhibitory concentrations of heme prior to subculture. The inclusion of this secondary counterscreen can, in some aspects, rule out compounds that non-specifically increase the expression of the XylE and Lux-based reporter genes.

The toxicity of candidate compounds can be evaluated using a mitochondrial dehydrogenase assay (MDA) system on several cell lines from distinct human organs. MDA employs a spectrophotometric measurement of cellular viability as a function of mitochondrial dehydrogenase activity with 3-[4,5-dimethylthiazol-2-yl]-2,5-diphenyl tetrazolium bromide (MTT) substrate. If cells are viable, mitochondrial dehydrogenases cleave the tetrazolium ring of MTT leading to the formation of purple MTT formazan crystals. Greater production of MTT formazan correlates with a larger number of viable cells and the formazan product is assayed by absorbance at 570 nm. This assay has been used extensively for measurements of mammalian cell viability and proliferation (Benimetskaya, L., N. Guzzo-Pernell, S. T. Liu, J. C. Lai, P. Miller, and C. A. Stein. 2002. "Protamine-fragment peptides fused to an SV40 nuclear localization signal deliver oligonucleotides that produce antisense effects in prostate and bladder carcinoma cells." Bioconjug Chem 13:177-187; Chi, K. C., A. E. Wallis, C. H. Lee, D. L. De Menezes, J. Sartor, W. H. Dragowska, and L. D. Mayer. 2000. "Effects of Bcl-2 modulation with G3139 antisense oligonucleotide on human breast cancer cells are independent of inherent Bcl-2 protein expression." Breast Cancer Res Treat 63:199-212).

The toxicity of compounds of interest can be determined using MDA and compared to known standards. Compounds demonstrating appreciable cytotoxicity can, in some aspects, be excluded as viable therapeutics; however cytotoxicity does not preclude these compounds from having utility as reagents for probing the mechanism of *staphylococcal* heme sensing.

4. XylE Reporter Assay

*S. aureus* strains harboring the appropriate reporter construct were inoculated into 500 µl of TSB containing 10 µg/ml chloramphenicol in 1.5 ml tubes. Cultures were grown O/N at 37° C. with shaking. Bacteria were pelleted by centrifugation and spent medium was aspirated. The pellet was washed once with 500 µl of 20 mM potassium phosphate, pH 7.6, and resuspended in 150 µl of 100 mM potassium phosphate buffer, pH 8.0, 10% (v/v) acetone, 25 µg/ml lysostaphin. After 20 minute incubation at 37° C. and 5 minute incubation on ice, samples were centrifuged at 20,000 g for 30 minutes at 4° C. 1-10 µl of supernatant was added to a 96-well plate and 200 µl of 100 mM potassium phosphate, pH 8.0, 0.2 mM pyrocatechol was added to each well. Formation of 2-hydroxymuconic semialdehyde was tracked by measuring the absorbance at 375 nm every minute for 30 minutes on a Varian MP 50 microplate reader. Protein concentration in samples was determined by BCA (Pierce). One unit of specific activity of XylE in a sample is defined as the formation of 1 nmol of 2-hydroxymuconic semialdehyde per minute per milligram of cellular protein at 30° C. (Chien, Y., Manna, A. C., Projan, S. J., and Cheung, A. L. 1999, "SarA, a global regulator of virulence determinants in *Staphylococcus aureus*, binds to a conserved motif essential for sar-dependent gene regulation. J. Biol. Chem. 274, 37169-37176).

5. Construction of a HrtAB Promoter-xylE Reporter

The hrtAB intergenic region was fused to the xylE structural gene by PCR-SOE. In the first reaction, primer P1B: CCCCGAATTCGCACCATAGCTATAAACTCC and P2B: CCTTTGTTCATATCGATTCACTTCTCC were used to amplify the hrtAB intergenic region from *S. aureus* strain Newman genomic DNA. In the second PCR reaction primers P3B:GTGAATCGATATGAACAAAGGTGTAATGCG and P4B:CCCGGATCCATACCATCAGGTCAGCACGG were used to amplify the xylE structural gene using pALC1639 template DNA (provided by Dr. Ambrose Cheung) and PCR product purified using a Qiagen gel extraction kit. For the PCRSOE reaction, a 1:300 dilution of purified reaction 1 and reaction 2 PCR products was mixed and amplified by PCR using P1A and P4A. This yielded a construct in which the hrtAB intergenic region is fused to the xylE gene in such a manner that the position of the start codon for xylE corresponds to the position of the start codon for hrtB in the hrtAB locus. The hrtAB promoter-xylE fusion DNA was then subcloned into pOS1. As a control we also constructed a promoterless xylE vector. The xylE gene was amplified from pACL1639 template DNA using the primers P1C: CCCGAATTCATGAACAAAGGTGTAATGC and P2C: CCCGGATCCATACCATCAGGTCAGCACGG and then cloned into the pOS1 vector.

6. RT-PCR

*S. aureus* cultures were grown O/N at 37° C. with shaking in 5 mls of RPMI containing 1% casamino acids with or without different hemin concentrations. One ml of the O/N cultures was then sedimented and the bacterial pellet treated with RNA protect Bacteria Reagent (Qiagen). Cells were then incubated with lysostaphin for 10 minutes at 37° C. to remove the bacterial cell wall. Total RNA was then isolated from bacterial protoplasts using the RNA easy kit (Qiagen). Total RNA was examined via absorbance (Abs 260/280) and by agarose gel electrophoresis. Two µg of total RNA were used for the reverse transcription reaction using M-MLV reverse transcriptase (Promega) and random hexamers primers (Applied Bbioscience). The RT-reaction product was then diluted 1:200 and used for a PCR reaction using specific primers for the hrtA transcript (ABC2-5-RT:TAAACAGCATCGTC-CTAGTG and ABC-3-RT:CAAATAATCTTCGATCGT-GTG) and the 16srRNA transcript (16srRNA-5-RT:GC-GAAGAACCTTACCAAATC and 16srRNA-3-RT: CCAACATATCACGACACG). PCR amplicons were then analyzed by agarose gel electrophoresis.

7. Bacterial Strains

*S. aureus* Newman, a human clinical isolate, can be used in in connection with the disclosed methods and compositions (Duthie, E. S., and Lorenz, L. L. 1952, "Staphylococcal coagulase; mode of action and antigenicity." J. Gen. Microbiol. 6, 95-107). The ΔsrtA mutant strain has been previously described (Mazmanian, S. K., Liu, G., Jensen, E. R., Lenoy, E., and Schneewind, O. 2000, "*Staphylococcus aureus* sortase mutants defective in the display of surface proteins and in the pathogenesis of animal infections." Proc. Natl. Acad. Sci. U S A 97, 5510-5515; Mazmanian, S. K., Liu, G., Ton-That, H., and Schneewind, O. 1999 "*Staphylococcus aureus* sortase, an enzyme that anchors surface proteins to the cell wall," Science 285, 760-763). Erythromycin cassette insertion mutants of the hrtA, hrtB, and hssS genes were obtained from the Phoenix (N) library, clones PhiNE 03177 (SAV2359), PhiNE 01762 (SAV2360), PhiNE 01562 (SAV2362), and PhiNE 07744 (SAV2362) (Bae, T., Banger, A. K., Wallace, A., Glass, E. M., Aslund, F., Schneewind, O., and Missiakas, D. M. 2004, "*Staphylococcus aureus* virulence genes identified by bursa aurealis mutagenesis and nematode killing." Proc. Natl. Acad. Sci. USA 101, 12312-12317). The Phoenix (N) library mutants were transduced into Newman. The ΔhrtA and ΔhssR isogenic mutant strains were generated by deletion of the genes following a protocol described by Bae and Schneewind (Bae, T., and Schneewind, O. 2005, "Allelic replacement in *Staphylococcus aureus* with inducible counter-selection." Plasmid). To create a complementation vector coding for wildtype hrtA, the hrtAB intergenic region containing the predicted promoter sequence for hrtAB was fused to the hrtA coding sequence by polymerase chain reaction sequence overlap extension (PCR-SOE) (Horton, R. M., Cai, Z. L., Ho, S. N., and Pease, L. R. 1990, "Gene splicing by overlap extension: tailor-made genes using the polymerase chain reaction," Biotechniques 8, 528-535).

8. Growth Curve Assay

*S. aureus* cultures were grown overnight (O/N ~15 hrs) at 37° C. with shaking at 180 RPM in tryptic soy broth (TSB). Cultures were diluted 1:75 and inoculated into roundbottom 96-well plates in a final volume of 150 µl. Cultures were grown at 37° C. with aeration and bacterial growth was monitored by the increase in absorbance (O.D.600) over time. For the hemin adaptation assays, the medium was supplemented with different hemin concentrations prior to bacterial inoculation. The results represent the mean±S.D. from triplicate determinations and the asterisks denote statistically significant differences as determined by Student's t test ($p<0.05$).

9. Mouse Model of Infection

Seven to eight week old female BALB/c mice (Jackson Laboratories) were infected with $1 \times 10^6$ colony forming units by i.v. injection into the retro-orbital vein complex using methods known in the art. *S. aureus* wildtype, ΔhrtA or ΔhssR mutant strains were used in these infections. Four days after infection, mice were euthanized with $CO_2$. Spleen, livers, and kidneys were removed, analyzed for abscess formation, homogenized in PBS, and *staphylococcal* load determined by colony formation on tryptic soy agar (TSA). Ten or more mice were infected with each strain of *S. aureus*. Statistical analyses were performed using the Student's t test. Mouse infections were approved by Vanderbilt University's Institutional Animal Care and Use Committee (IACUC). All experiments conform to regulatory guidelines for animal infections.

10. Inactivation of HssRS or HrtAB

To test the role of HssRS heme sensing and concomitant HrtAB expression in *S. aureus* pathogenesis, mice were infected intravenously with *S. aureus* wildtype, ΔhrtA, or ΔhssR. Animals infected with wildtype *S. aureus* exhibited overt signs of disease characteristic of *staphylococcal* infection. All animals infected with *S. aureus* ΔhrtA or ΔhssR appeared more moribund than those infected with wildtype as evidenced by a complete absence of mobility, a pronounced hunched posture, and extensive tremors. Autopsies conducted 96 hours postinfection revealed abscess formation in the kidneys of mice infected with any of the three *staphylococcal* strains. In contrast, only mice infected with *S. aureus* ΔhrtA or ΔhssR developed abscesses in the liver. Enumeration of bacterial loads in the livers of infected animals revealed a 2-3 log increase in the number of mutant *staphylococci* as compared with wildtype. This increase in virulence was liver-specific, since no difference was detected in the ability of the mutant strains to colonize the spleen or kidney compared to wildtype. The increased liver-specific hypervirulence of *S. aureus* ΔhrtA and ΔhssR is not due to intrinsically faster growth rates, because mutant strains exhibit similar growth kinetics to wildtype in laboratory growth conditions. Histological examination of livers infected with the mutant *staphylococci* revealed that hepatic hypervirulence occurs despite the recruitment of polymorphonuclear (PMN) cells. More specifically, the ΔhrtA or ΔhssR-induced abscesses were characterized by collections of purulent material containing PMNs, injured hepatocytes, and dense fibrous tissue. Together, these findings demonstrate that *S. aureus* strains lacking HssRS or HrtAB exhibit increased hepatic virulence.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A method for activating a heme sensor system in at least one bacterium comprising the step of contacting the at least one bacterium with an effective amount of a compound selected from the following compounds,

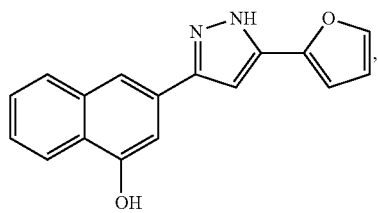

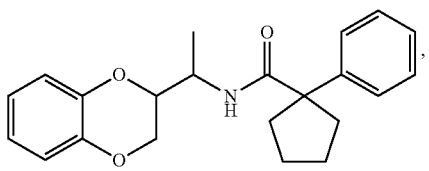

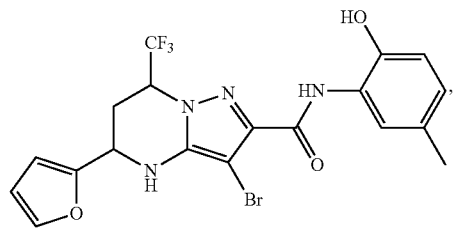

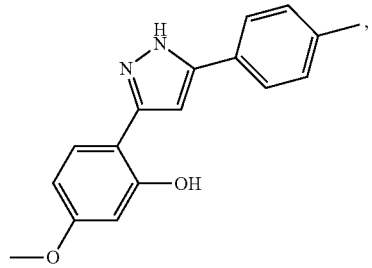

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Note = Synthetic Construct
<220> FEATURE:
<221> NAME/KEY: misc_feature
<222> LOCATION: 10-11
<223> OTHER INFORMATION: n=a,g,c or t (u)

<400> SEQUENCE: 1
gttcatattn ngttcatatt                                              20

-continued

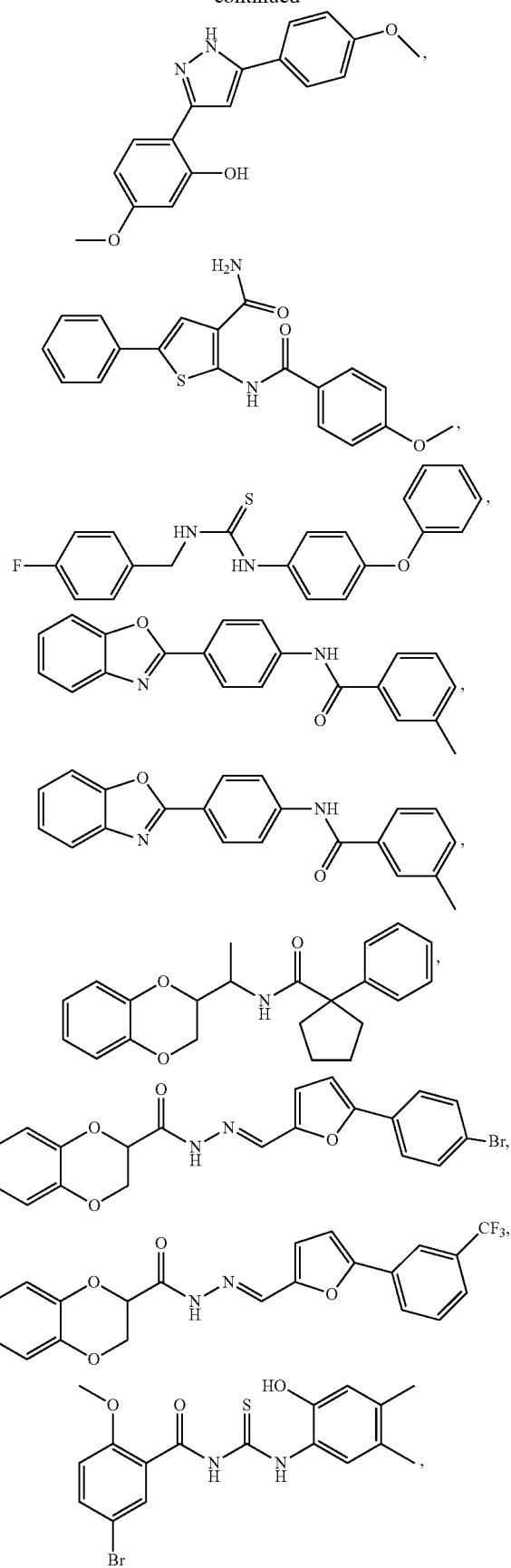

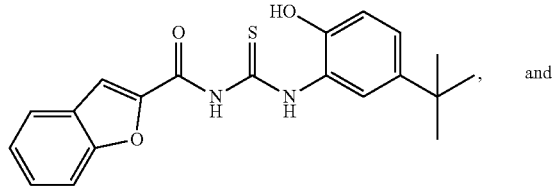

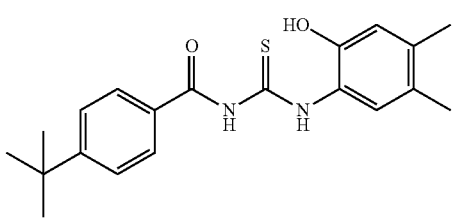

thereby activating a heme efflux pump (HrtAB) in the at least one bacterium.

2. The method of claim 1, wherein the bacterium is a gram-positive bacterium.

3. The method of claim 1, wherein the bacterium is a gram-positive pathogen.

4. The method of claim 1, wherein the bacterium is selected from *Bacillus anthracis, Bacillus cereus, Listeria monocytogenes, Listeria innocua, Enterococcus faecalis, Staphylococcus aureus, Staphylococcus epidermidis, Staphylococcus haemolyticus, Staphylococcus saprophyticus*, and *Lactococcus lactis*.

5. A method for treating a bacterial infection in a mammal comprising the step of administering a therapeutically effective amount of a compound selected from the following compounds,

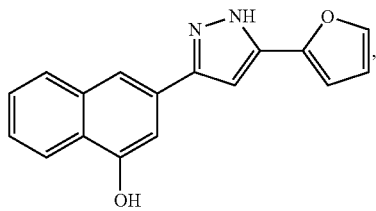

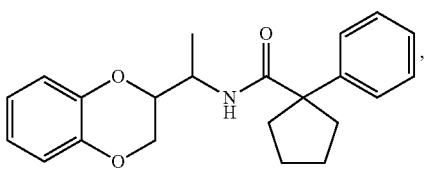

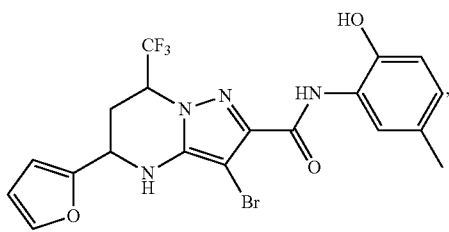

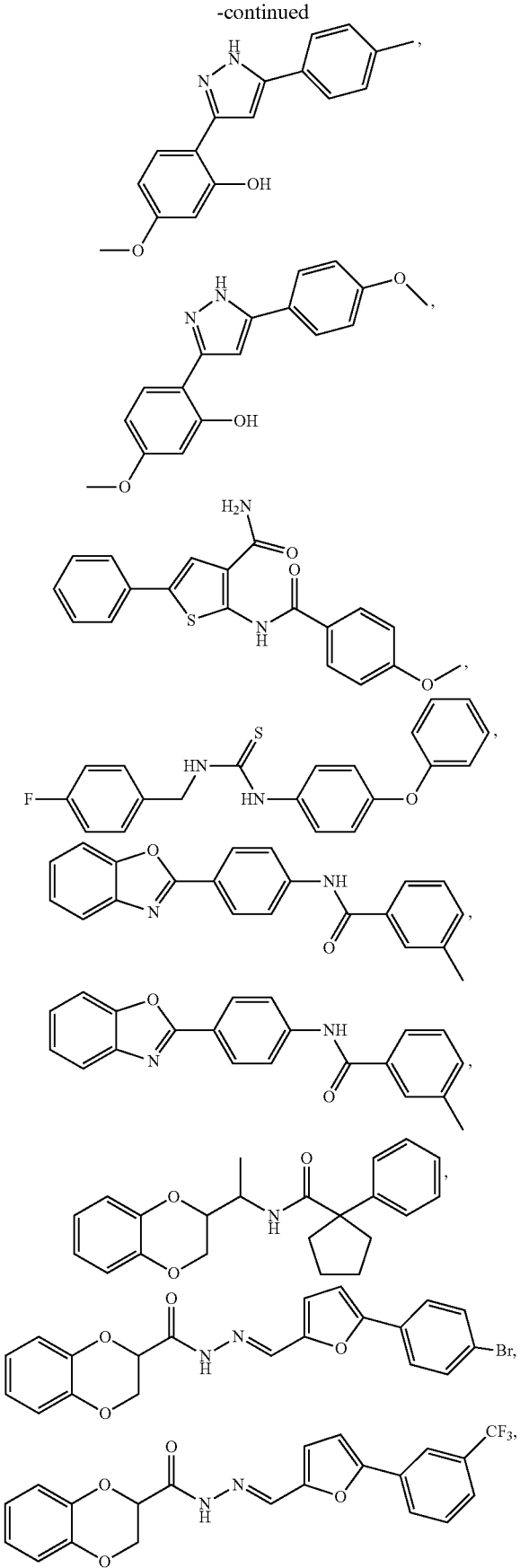

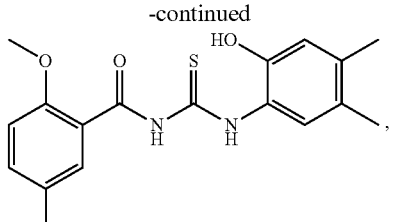

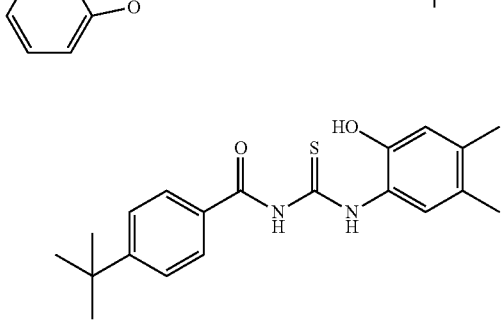

thereby decreasing bacterial virulence in the mammal.

6. The method of claim 5, wherein the mammal is a human.

7. The method of claim 5, wherein the mammal has been identified with a need for treatment of a bacterial infection prior to the administration step.

8. The method of claim 5, wherein the mammal has been diagnosed with the bacterial infection prior to the administration step.

9. The method of claim 5, further comprising the step of administering to the mammal a therapeutically effective amount of one or more antimicrobial agents.

10. The method of claim 5, wherein the compound is:

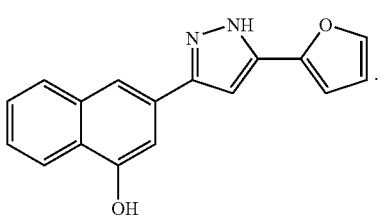

11. The method of claim 5, wherein the compound is:

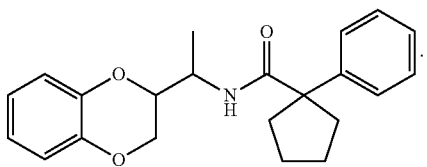

12. The method of claim 5, wherein the compound is:

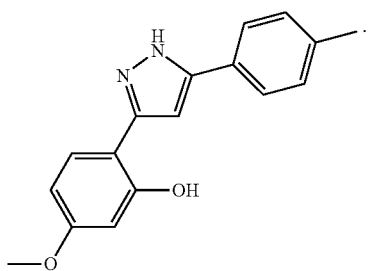

13. The method of claim 5, wherein the compound is:

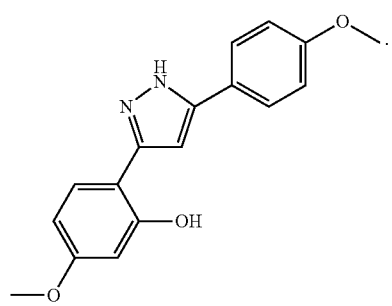

14. The method of claim 5, wherein the compound is:

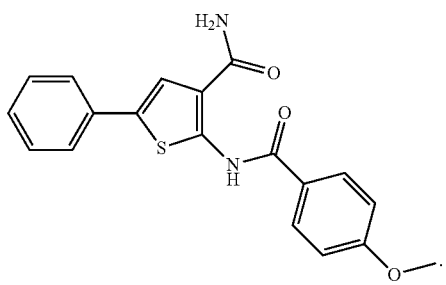

15. The method of claim 5, wherein the compound is:

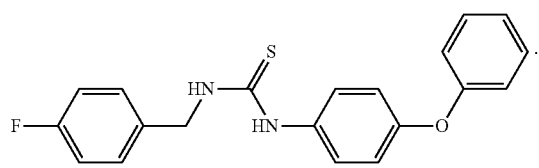

16. The method of claim 5, wherein the compound is:

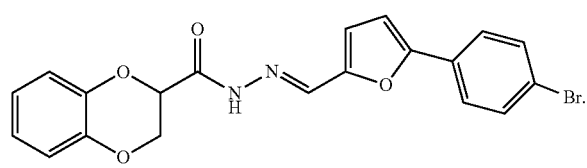

17. The method of claim 5, wherein the compound is:

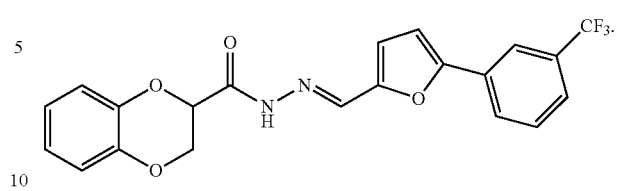

18. The method of claim 5, wherein the compound is:

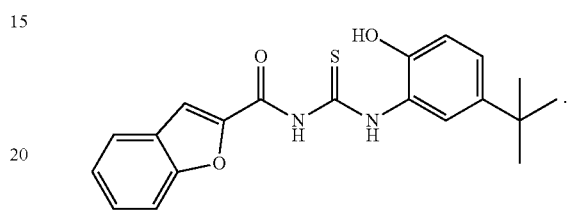

19. The method of claim 1, wherein the compound is selected from:

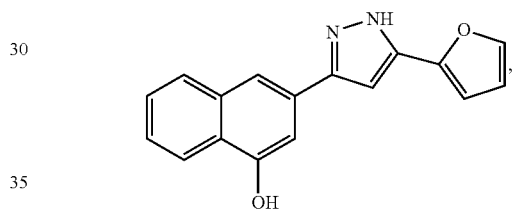

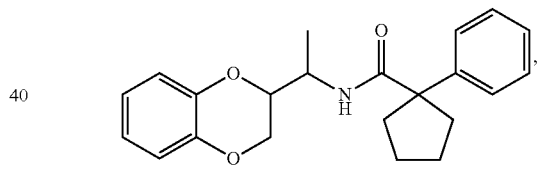

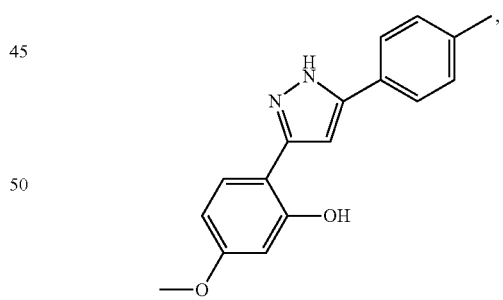

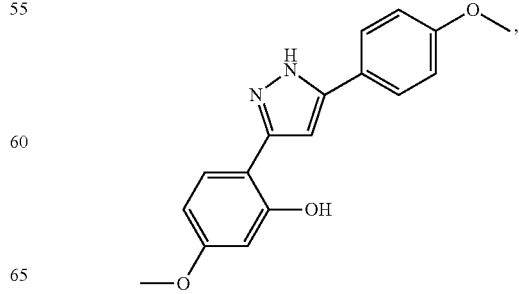

-continued
115
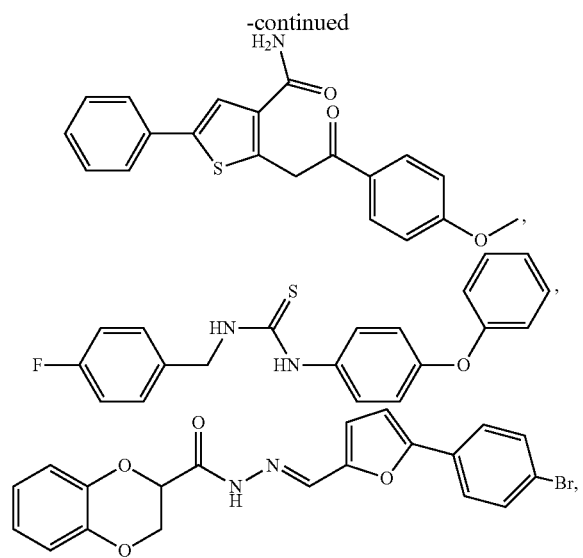
116
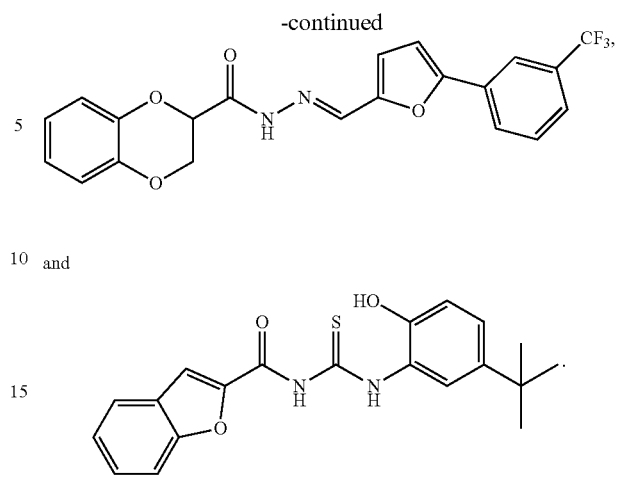
* * * * *